United States Patent [19]

Lopez

[11] Patent Number: 5,281,206
[45] Date of Patent: Jan. 25, 1994

[54] NEEDLE CONNECTOR WITH ROTATABLE COLLAR

[75] Inventor: George A. Lopez, Corona del Mar, Calif.

[73] Assignee: ICU Medical, Inc., Irvine, Calif.

[21] Appl. No.: 747,010

[22] Filed: Aug. 19, 1991

Related U.S. Application Data

[60] Continuation-in-part of Ser. No. 346,193, Jan. 9, 1987, abandoned, which is a division of Ser. No. 606,679, May 3, 1984, abandoned, which is a continuation-in-part of Ser. No. 543,248, Oct. 19, 1983, abandoned, which is a continuation-in-part of Ser. No. 460,585, Jan. 24, 1983.

[51] Int. Cl.$^5$ ............................................. A61M 25/00
[52] U.S. Cl. ..................................... 604/283; 604/905
[58] Field of Search ................... 604/86, 88, 192, 283, 604/284, 411–415, 905

[56] References Cited

U.S. PATENT DOCUMENTS

| | | |
|---|---|---|
| 1,578,517 | 3/1926 | Hein . |
| 2,210,098 | 8/1940 | Ravenscroft . |
| 2,999,499 | 9/1961 | Willet . |
| 3,502,097 | 3/1970 | Muller . |
| 3,630,199 | 12/1971 | Gangarosa et al. . |
| 3,797,486 | 3/1974 | Shaps . |
| 3,861,388 | 1/1975 | Vaughn . |
| 3,976,073 | 8/1976 | Quick et al. . |
| 3,986,508 | 10/1976 | Barrington . |
| 3,994,293 | 11/1976 | Ferro . |
| 4,005,710 | 2/1977 | Zeddies et al. . |
| 4,019,512 | 4/1977 | Tenczar . |
| 4,040,420 | 8/1977 | Speer . |
| 4,187,846 | 2/1980 | Lolachi et al. . |
| 4,191,183 | 3/1980 | Mendelson . |
| 4,214,779 | 7/1980 | Losell . |
| 4,219,912 | 9/1980 | Adams . |
| 4,257,416 | 3/1981 | Prager . |
| 4,294,249 | 10/1981 | Sheehan et al. . |
| 4,296,949 | 10/1981 | Muetterties et al. . |
| 4,306,705 | 12/1981 | Svensson . |
| 4,328,802 | 5/1982 | Curley et al. . |
| 4,329,987 | 5/1982 | Rogers et al. . |
| 4,338,933 | 7/1982 | Bayard et al. . |
| 4,362,156 | 12/1982 | Feller, Jr. et al. . |
| 4,439,193 | 3/1984 | Larkin . |
| 4,457,749 | 7/1984 | Bellotti et al. . |
| 4,673,400 | 6/1987 | Martin . |
| 4,810,241 | 3/1989 | Rogers . |
| 4,834,716 | 5/1989 | Ogle, II . |
| 4,946,445 | 8/1990 | Lynn ................................ 604/192 |
| 4,964,855 | 10/1990 | Todd et al. . |
| 4,998,713 | 3/1991 | Vaillancourt . |

FOREIGN PATENT DOCUMENTS

| | | |
|---|---|---|
| 0367549 | 5/1990 | European Pat. Off. . |
| 0438909 | 7/1991 | European Pat. Off. . |
| 855319 | 11/1952 | Fed. Rep. of Germany . |

Primary Examiner—John D. Yasko
Assistant Examiner—Anthony Gutowski
Attorney, Agent, or Firm—Knobbe, Martens, Olson & Bear

[57] ABSTRACT

A safety connector is provided for connection to the branch port on a fluid flow line. The connector comprises a tubular body having an opening at its distal end to receive a branch port and a channel in the wall of the tubular body adjacent to the distal end. The channel is adapted to receive the fluid flow line when the branch port is engaged within the tubular body. The connector also comprises a locking rotatable collar located on the distal end of the tubular body. The collar is rotatable from a first position wherein the channel is adapted to receive the fluid flow line when the branch port is engaged within the tubular body, and a second position wherein the collar prevents the removal of the branch port from the tubular body.

2 Claims, 13 Drawing Sheets

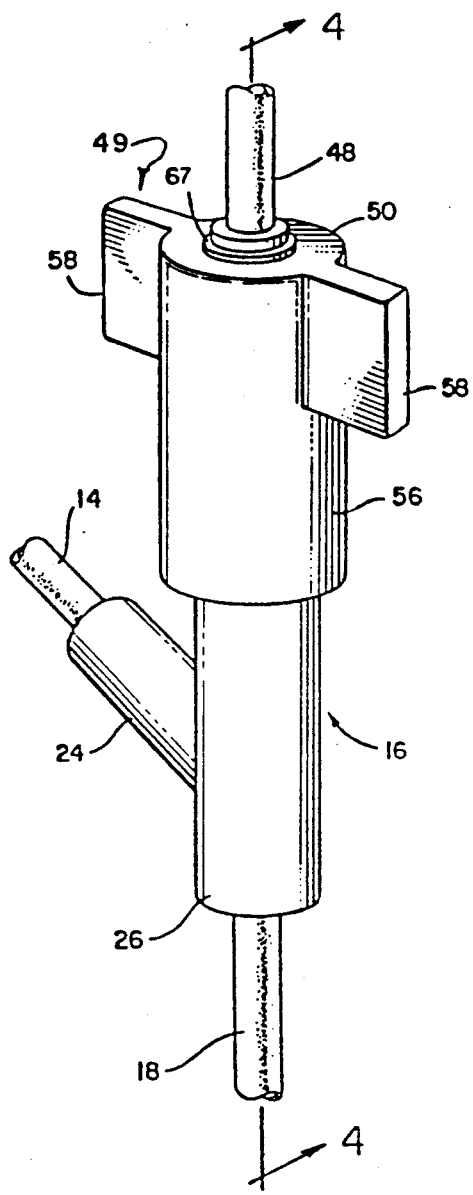
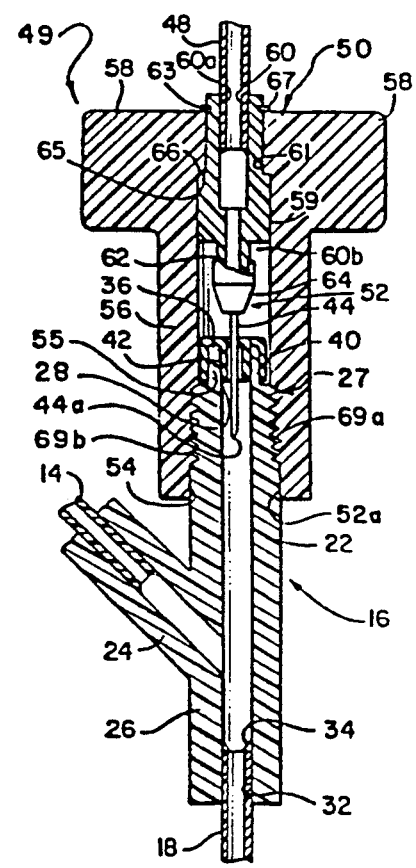
FIGURE 3
FIGURE 4
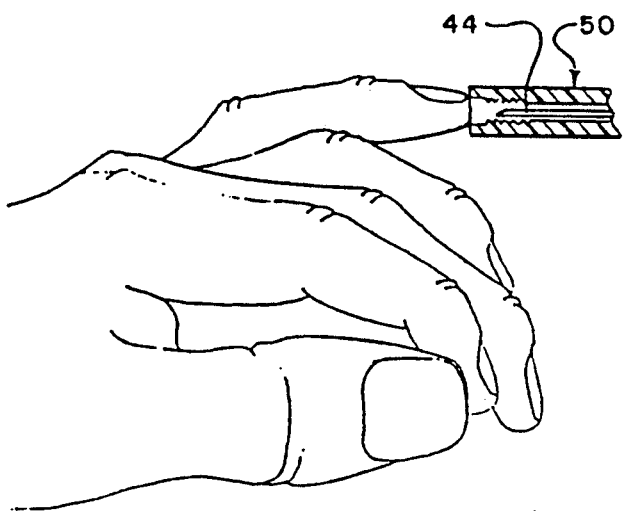
FIGURE 4a

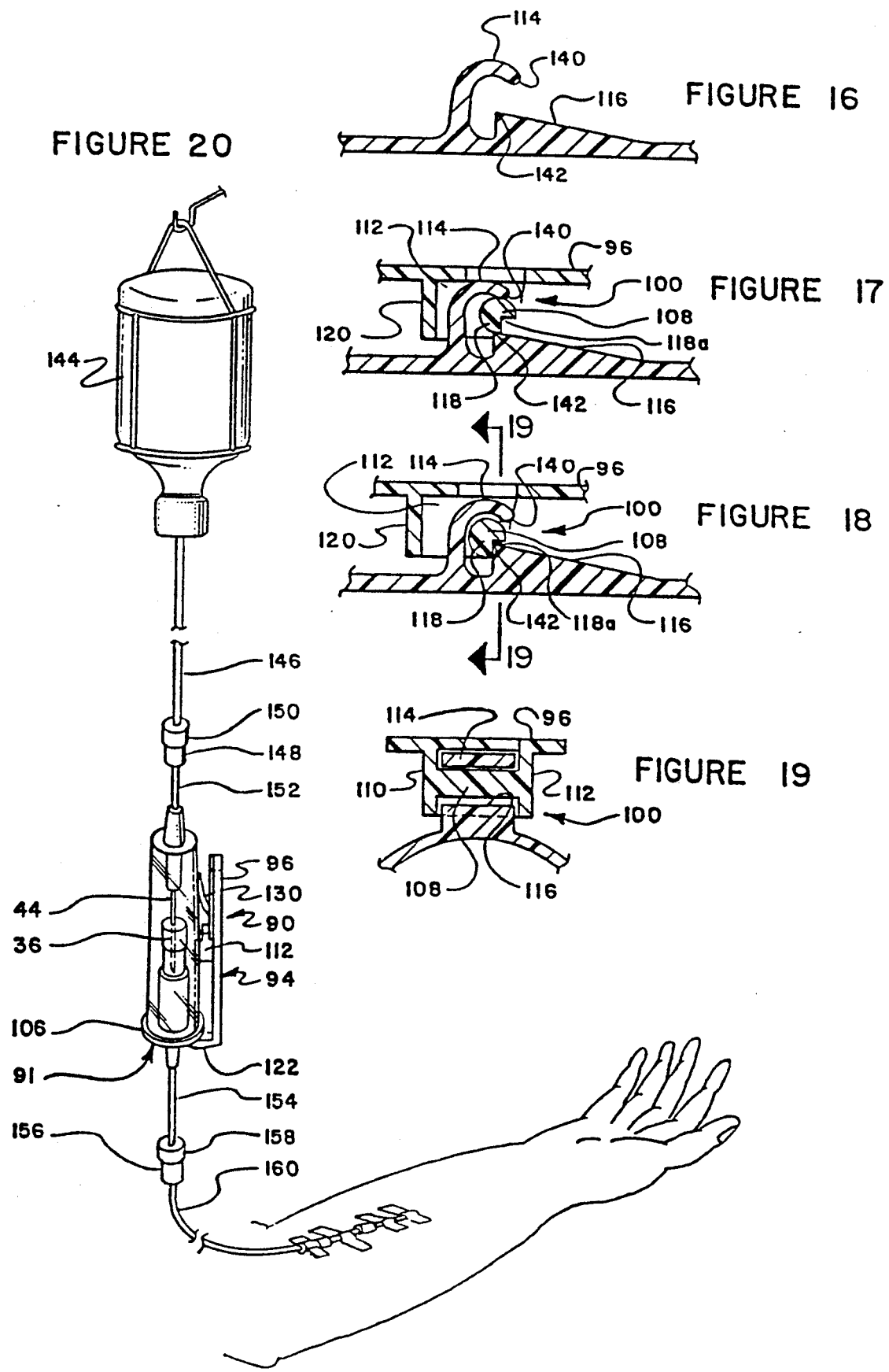

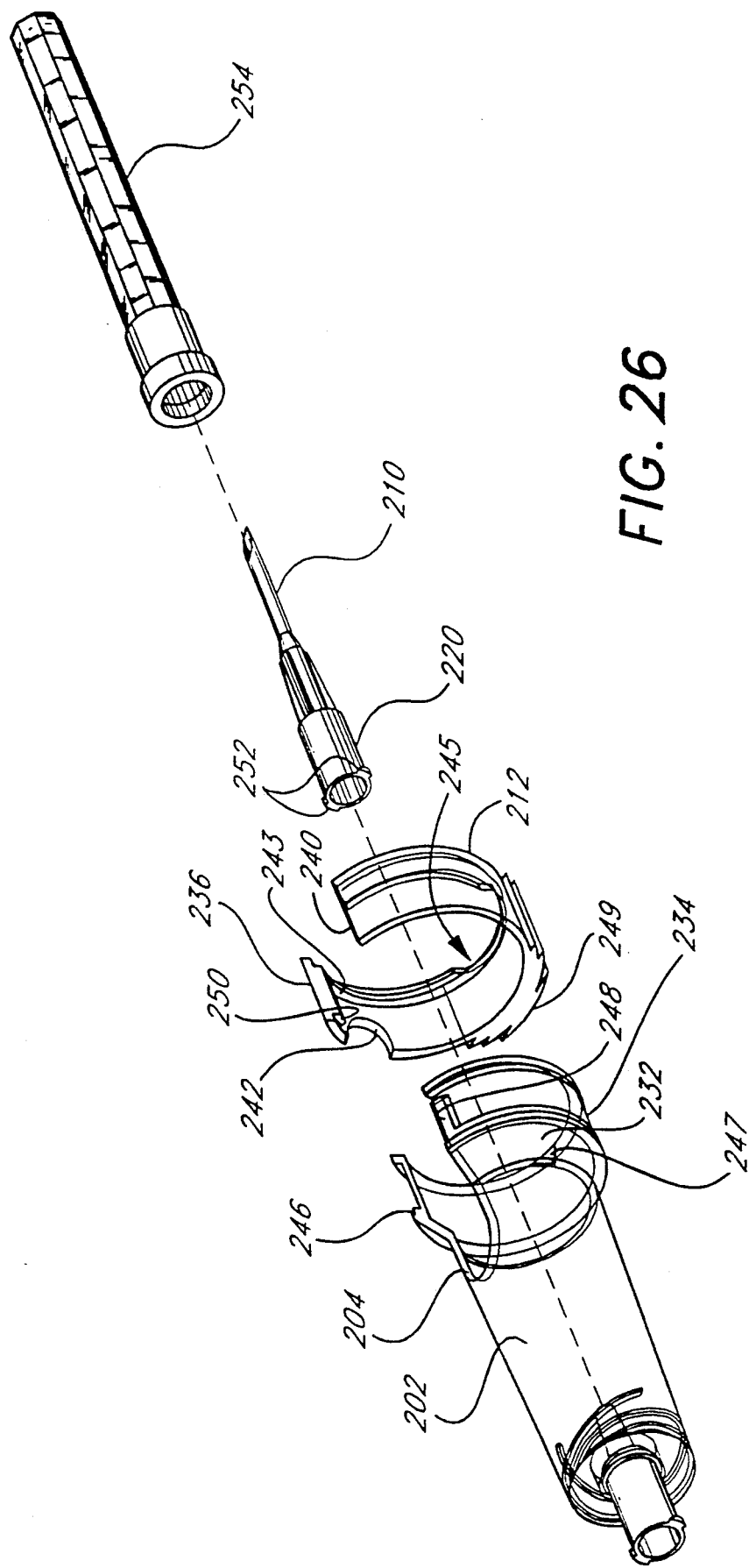

NEEDLE CONNECTOR WITH ROTATABLE COLLAR

RELATED PATENT APPLICATIONS

This application is a continuation-in-part of U.S. patent application Ser. No. 346,193, filed Jan. 9, 1987, (now abandoned) which is a division of U.S. patent application Ser. No. 606,679, filed May 3, 1984, and entitled "Medical Connector," now abandoned, which was a continuation-in-part application of U.S. patent application Ser. No. 543,248, filed Oct. 19, 1983, (now abandoned) and entitled "Medical Connector System," which was a continuation-in-part application of U.S. patent application Ser. No. 460,585, filed Jan. 24, 1983, and entitled "Device for Intravenously Introducing Medication Into a Patient, " (now abandoned). These previously filed patent applications are incorporated herein by reference and made part of this patent application.

BACKGROUND OF THE INVENTION

1. Field of the Invention

This invention relates to medical connectors used in the treatment of the injured or sick, and in particular to a connector for introducing medication into a patient in a safe, convenient way.

2. Background Discussion

It is a common practice in treating patients, particularly patients who must be cared for under emergency conditions, with medication introduced into the patient intravenously. An intravenous solution, commonly referred to as parenteral liquid, is fed from a container holding this liquid. The liquid flows through tubing into a needle which has been inserted into the patient's vein. The needle is taped securely to the patient's body and is not likely to pull loose if the patient moves. Medication needed to sustain the life of the patient, for example, drugs which maintain the blood pressure of the patient at the desired level, are added to the parenteral liquid. The conventional practice is to introduce the medication through a second needle inserted into a sealed entry port in the tubing through which the parenteral liquid flows.

One problem with this conventional practice is that the needle may be pulled loose from the sealed port relatively easily. Such accidental removal of the needle from the sealed port can have very serious consequences and could even lead to the death of the patient. Although many hospitals require nurses to tape the needle securely to the tubing, this is not always done, because taping is a burdensome and time consuming task.

A second problem with the conventional practice is needle sticks. From time to time a nurse in attempting to insert the needle into the sealed entry port will accidentally stick himself or herself with the needle. This often occurs under emergency conditions when the nurse is under pressure to complete this task as quickly as possible. Not only is the accomplishment of the task delayed but the nurse must stop working and have a blood test performed. Such a test is needed in case the nurse becomes infected, because the hospital will be responsible financially. Consequently, needle sticks not only result in increased hospital cost, but are a possible life threatening event to the nurse.

A third problem with the conventional practice is infection. All too often a patient's life is seriously endangered by bacteria gaining entry into a patient's blood stream and establishing an infection. In a vast number of cases it is unknown how the bacteria gain entry. We have observed conditions in hospitals and identified that one likely way the bacteria gain entry is by contamination of the needle inserted into the sealed entry port. This happens when the nurse notices that the needle has been pulled loose and simply reinserts it even though it may now have on its surface bacteria picked up by direct contact with, for example, the patient's bedding. Another possible way that bacteria may gain entry into the patient's blood stream is through contamination of the tape used to hold the needle to the connector.

SUMMARY OF THE INVENTION

The present invention provides a safety connector for connection to the branch port on a fluid flow line having a branch port thereon. The connector comprises a tubular body having an opening at the distal end thereof for receiving the branch port; a channel in the wall of the tubular body, adjacent the distal end thereof, for receiving the fluid flow line when the branch port is engaged within the tubular body; and a locking collar rotatably disposed on the distal end of the tubular body, the collar rotatable from a first position in which the channel is adapted to receive the fluid flow line when the branch port is engaged within the tubular body, and a second position in which the collar prevents removal of the branch port from the tubular body. Preferably, the branch port is on a piggyback connector of the type adapted for combining the fluid flow from two different sources of parenteral fluids, and the two influent lines and the one effluent line of the piggyback connector are arranged in a substantially Y-shaped configuration. The branch port preferably comprises a generally tubular shaped body having a pierceable septum thereon. In a preferred embodiment, the safety connector also includes a luer connection on the interior of the tubular body at the proximal end thereof for receiving the hub of a hollow needle which, when installed, extends distally within the tubular body. In this preferred embodiment, the distal end of the needle is disposed within the tubular body at a sufficient distance from the distal end thereof so as to substantially prevent contact between the distal end of the needle and the fingers of an operator handling the safety connector.

Another aspect of the present invention provides a method of securing a second influent fluid line to the branch port on a generally Y-shaped piggyback connector, the connector having a first influent fluid line on one side of the Y-shaped connector and a pierceable septum on the other side of the Y-shaped connector. This method comprises the following steps: providing a safety connector of the type having a generally tubular body with a needle therein adapted to engage the pierceable septum on the branch port; advancing the tubular connector in the direction of the branch port so that the needle within the connector pierces the septum on the branch port and the first influent line is received within an axially extending slot in the wall of the connector; and rotating a rotatable collar on the distal end of the connector to form an enclosure around the first influent line, thereby maintaining the second fluid line in fluid communication with the piggyback connector, and substantially preventing the retraction of the port from the tubular body. The rotatable collar is preferably rotatable between a first position in which the axially extending slot is open to the distal end of the wall for receiving the first influent line, and a second position wherein the distal end of the axially extending slot is occluded, thereby preventing the removal of the first influent line in an axial direction. The rotatable collar preferably provides aural and tactile feedback to the user when the rotatable collar is moved from the first position into the second position.

In yet another aspect of the present invention, a safety connector for placing an influent fluid line in fluid communication with an effluent fluid line is provided. This effluent fluid line has a pierceable septum thereon and a projection extending radially therefrom proximate the pierceable septum. The connector comprises an elongate tubular body having proximal and distal ends thereon; a needle removably disposed in the tubular body, the needle having a proximal attachment end and a sharpened distal end, the proximal end of the needle secured to the proximal end of the tubular body, the needle extending in the distal direction within the tubular body; a slot in the wall of the tubular body extending axially from the distal end in the direction of the proximal end, the slot adapted to receive the projection on the fluid line; and a rotatable collar disposed on the distal end of the tubular body, the collar adapted to rotate between a first position in which the slot is unobstructed so that the projection may be introduced therein when the pierceable septum on the effluent fluid line is engaged by the needle, and a second position in which the distal end of the slot is obstructed to substantially prevent the removal of the projection therefrom, thereby preventing removal of the needle from engagement with the pierceable septum. This safety connector preferably includes a recess on the tubular body for receiving a projection on the collar when the collar is in the second position, thereby producing an audible click when the collar is rotated to dispose the projection within the recess. The projection preferably comprises an axially oriented ridge which extends radially inwardly from the collar. The safety connector also preferably includes a substantially cylindrical surface on the exterior distal end of the tubular body for slidably receiving the rotatable collar. Preferably, the cylindrical surface comprises at least one annular shoulder thereon for receiving a radially inwardly extending annular flange on the rotatable collar to rotatably secure the collar to the surface. In one embodiment, the rotatable collar further comprises friction enhancing structures on the exterior surface thereof. Preferably, the rotatable collar is provided with a discontinuity which, when aligned with the slot in the wall of the tubular body, provides an axially extending slot for receiving the projection in an axial direction, wherein rotation of the rotatable collar from the first position into the second position rotates the discontinuity in the collar out of alignment with the slot in the wall of the tubular body, thereby entrapping the projection and preventing axial withdrawal of the effluent fluid line. This embodiment of the invention also preferably includes a male luer connector on the exterior of the proximal end of the tubular body. In a preferred embodiment, the tubular body is further provided with a radially outwardly extending stop which is received in a circumferential channel on the radially inwardly facing surface of the rotatable collar, the circumferential length of the channel providing limits to the range of rotation of the rotatable collar with respect to the tubular body.

MAJOR FEATURES OF THE INVENTION

The problems discussed in the BACKGROUND OF THE INVENTION present a serious health hazard to patients and their nurses. The present invention eliminates these problems and provides a medical connector which is both safe and convenient to use.

There are several features of this invention which contribute to its safety and convenience, no single one of which is solely responsible for these desirable attributes. Many of these features were present in our experimental versions of the invention, which were improved after testing. Without limiting the scope of this invention as expressed by the claims, its more prominent features will now be discussed briefly. After considering this discussion, and particularly after reading the section of this application entitled DETAILED DESCRIPTION OF THE DRAWING, one will understand how the features of this invention provide the attributes of safety and convenience.

One safety feature of this invention is the use of a cap member to enclose the needle to be inserted into the sealed entry port structure. This cap member fits snugly over the entry port structure, connecting with the port structure in a male-female mating relationship. The needle pierces the seal when the cap member is seated on the port structure. This needle is housed deep within a cavity in the cap member that terminates in an open mouth into which the sealed end of the port structure fits. This open mouth is narrow in width so that the finger of the nurse or patient cannot fit into the cavity and contact the needle. Since the needle is so mounted within the cap member, the likelihood of bacterial contamination is avoided or reduced and the nurse is protected against accidental needle sticks.

A second safety feature is provided by the wall design of the cap member and port structure. These walls are of preferably cylindrical configuration and engage each other like a telescope. The interior surface of the wall of the cap member slides over the exterior surface of the wall of the mating port structure, with these walls engaging each other to guide the needle into the center of the seal. This ensures that the needle does not scrape against the inside surface of the wall of the port structure. Particles scraped from this wall could make their way into the patient's blood stream and result in death. This potentially lethal condition is inherent in the design of conventional devices. But the connector of this invention, with the guideway wall design of the cap member and port structure, ensures that the needle is directed into the center of the seal so that it avoids scraping against the inside surface of the wall of the port structure. This guideway wall design also permits the nurse quickly to connect the cap member to the port structure. This makes the connector of this invention not only more convenient to use, but in emergencies, enables the nurse to administer medication to a patient faster than with conventional devices and doing it without the danger of needle sticks.

A third safety feature of the invention is that a locking mechanism detachably secures the cap member to the port structure. Because of this feature, movement of the patient does not result in accidental removal of the needle from the seal. Although many different types of locking mechanisms may be employed, the preferred one provides a sound upon locking engagement of the cap member and port structure. We have devised such a locking mechanism which produces a sound such as "click." This "click" is an audible signal which tells the nurse that the cap member is locked safely to the port structure and cannot be accidentally jarred loose by movement of the patient.

Several embodiments of the invention illustrating all the features of this invention will now be discussed in detail. These embodiments show the invention being used for administering medication intravenously to a patient. This invention may also be used to administer medication to a patient in other ways, for example, intracranially or intraperitoneally.

BRIEF DESCRIPTION OF THE DRAWINGS

The drawing, wherein the numerals indicate like parts, depicts four embodiments of this invention in which:

FIG. 3 is a perspective view of the first embodiment of the medical connector of the present invention which employs a slip-on/twist lock type means for securing the cap member to the port structure.

FIG. 4 is a cross-sectional view of the connector shown in FIG. 3 taken along line 4—4 of FIG. 3.

FIG. 4a is a perspective view showing how the cap member prevents needle sticks.

FIG. 16 is an enlarged cross-sectional view of a portion of the hinge of the locking mechanism.

FIG. 17 is an enlarged cross-sectional view of the position of the handle just prior to being secured to the cap member.

FIG. 18 is a cross-sectional view similar to that shown in FIG. 17 depicting the handle coupled to the cap member.

FIG. 19 is a cross-sectional view taken along line 19—19 of FIG. 18.

FIG. 20 is a perspective view showing the medical connector of FIG. 7 having one end coupled to a tube extending from a patient's arm and another end coupled to a tube extending from a container holding medication.

FIG. 26 is an exploded elevational view of the embodiment shown in FIG. 25.

DETAILED DESCRIPTION OF THE DRAWING

Conventional Connector System

Figure 1:
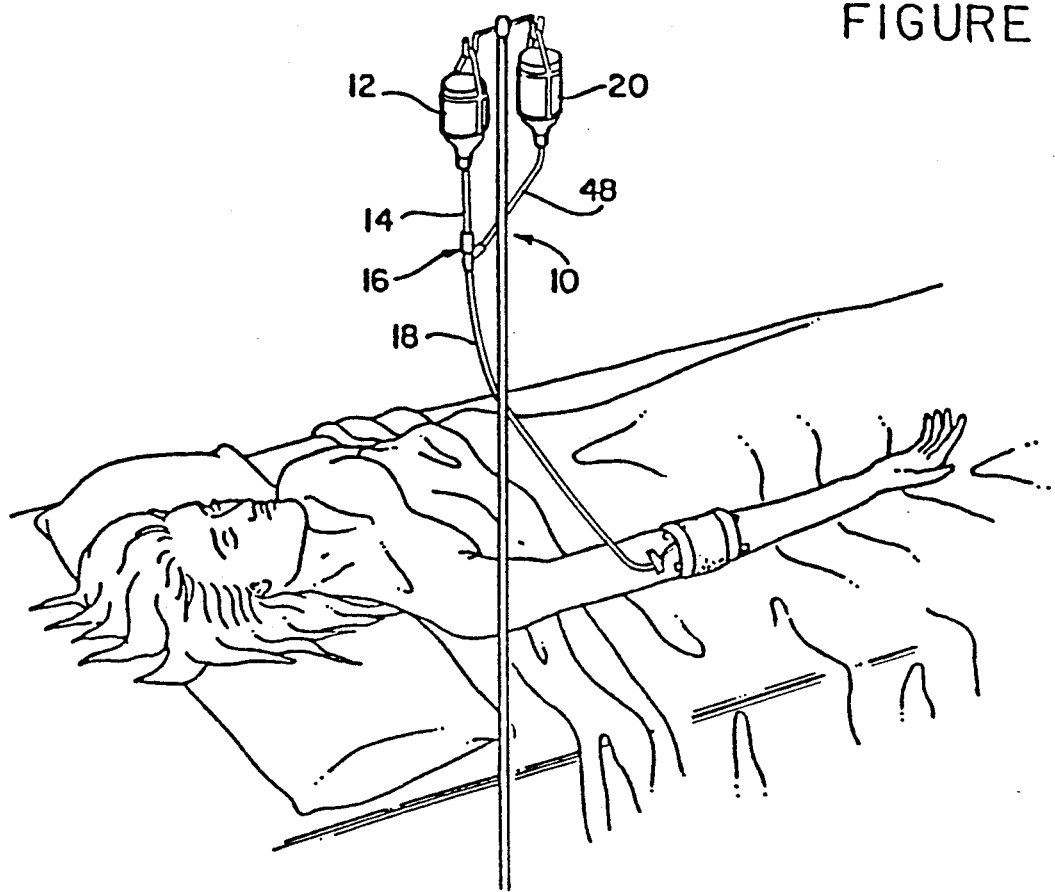
FIG. 1 is a schematic view illustrating administering medication intravenously to a patient in accordance with conventional practice.
Figure 2:
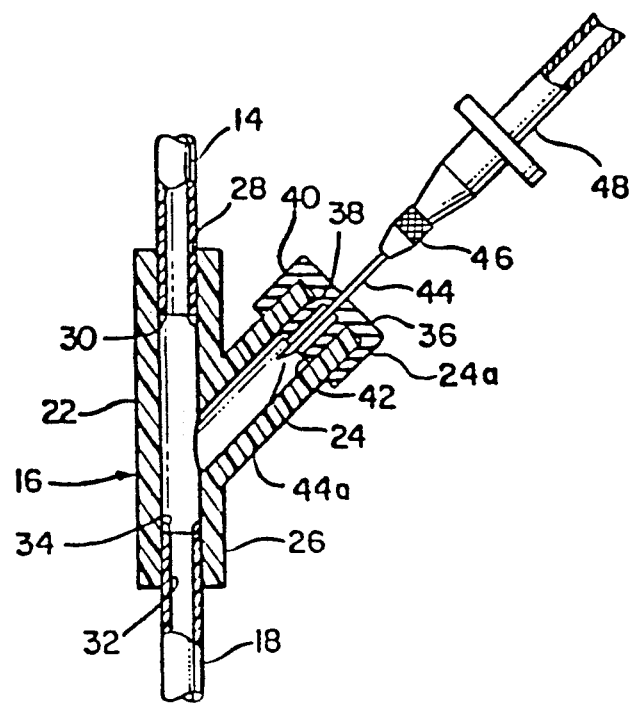
FIG. 2 is a cross-sectional view of a piggyback connector for introducing parenteral liquid and medication intravenously to the patient shown in FIG. 1.

As shown in FIGS. 1 and 2, the current way of intravenously introducing parenteral liquid into a patient is by the conventional feeding system 10. This feeding system 10 includes a container 12 for the parenteral liquid, a tube 14 extending from the container and connected to a Y or "piggyback" connector 16, and a tube 18 from the piggyback connector to a needle (not shown) inserted into a vein of the patient. The needle is taped to the patient so that movement of the patient will not result in the needle being pulled from the patient's vein.

As best illustrated in FIG. 2, medication from the container 20 is introduced through the piggyback connector 16 into the parenteral liquid flowing through the feeding system 10. This piggyback connector 16 consists of two tubular conduits 22 and 24 which merge into a third tubular conduit 26. The tubing 14 from the container 12 of parenteral liquid is inserted into the inlet port 28 of the conduit 22 and secured in position, for example, by an adhesive which bonds the external surface of this tube to the internal wall surface of the conduit. There is a stop 30 which limits the extent to which this tube 14 can be inserted into the conduit. In a similar fashion, the tube 18 is secured to the outlet port 32 of the piggyback connector. This tube 18 is inserted into the outlet port 32 until it abuts a stop 34 in the internal wall of the conduit. This tube 18 is secured by an adhesive to the internal wall of the conduit 26.

The sealed entry port structure of the conventional feeding system 10 is provided by the branch conduit 24 which has a standard latex rubber seal 36 at its inlet port 38 to seal this port. Consequently, bacteria cannot enter the piggyback connector 16 via the inlet port 38 because of the seal 36. This seal 36 is of conventional design and includes coaxial annular aprons 40 and 42 which fit over the conduit wall 24a and grip the external and internal wall surfaces to hold the seal securely to the conduit 24. A suitable seal may be obtained from the West Company of Phoenixville, Pennsylvania.

The medication is introduced into the parenteral liquid flowing through the piggyback connector 16 by a needle 44 which is inserted through the central part of the seal 36 into the branch conduit 24. This needle 44 is connected by a suitable connector 46 to a tube 48 which is connected to the container 20 (FIG. 1) for the medication. As parenteral liquid flows through the piggyback connector 16 into the inlet port 28 and out the outlet port 32, the medication is drawn into this stream of liquid, flowing from the container 20 via the tube 48 and through the open tip or end 44a of the needle 44 into the parenteral liquid.

After studying FIGS. 1 and 2, the several problems associated with the conventional practice can now be more fully understood. If the patient moves, for example, rolls or moves his or her arm, the needle 44 may be pulled from the seal 36. If this occurs, the latex seal 36 has sufficient resiliency to close off the hole in the seal produced by the needle 44. The parenteral liquid will continue to flow into the patient's system, but the necessary medication is no longer being introduced into it. The consequences of this condition are very grave and, if this condition is unnoticed by the nurse, it could result in the death of the patient or serious complications in the patient's treatment. Even if the nurse notices that the needle 44 has been removed from the seal 36 and reinserts it into the seal, it is possible that the needle has been contaminated with bacteria. The use of such a contaminated needle 44 is unacceptable, but nevertheless this sometimes happens. The needle 44 may be taped to the conduit 24, and many hospitals instruct nurses to do this. When this task is done, the needle 44 is secured, but cannot be conveniently removed and then reinserted. And even when taping the needle 44, if this is not done carefully, the needle may still be contaminated by the nurse touching the needle or the tape being contaminated. Also, because the nurse holds the conduit 24 with one hand while inserting the needle 44, the nurse may accidentally stick the needle directly into the hand holding this conduit, or stick the needle through the conduit wall 24a into this hand.

These problems associated with the conventional practice are eliminated by the several different embodiments of this invention disclosed hereinafter.

First Embodiment of the Invention

As illustrated in FIGS. 3 and 4, the first embodiment of this invention, connector 49, employs a cap member 50 housing deep within the needle 44. As will be discussed in greater detail hereinafter, the cap member 50 is secured by a slip-on/twist lock type of locking mechanism to the piggyback connector 16 so that movement of the patient does not result in the needle 44 being pulled from the seal 36. The parenteral liquid is introduced via the conduit 24, and the conduit 22 carries the seal 36 that covers the inlet port 28. In this embodiment, this sealed conduit 28 constitutes the entry port structure 27. The cap member 50, is detachably secured to the entry port structure 27, with the needle 44 penetrating the seal center of the seal 36 when the cap member 50 mates with the port structure 27.

The cap member 50 comprises a cylindrical connector section 56 having a hollow interior forming the chamber or cavity 52 housing the needle 44. This needle 44 is disposed lengthwise along the longitudinal axis of the cavity 52 and is centrally located. The cavity 52 has an open mouth 52a which allows the cap member to be seated over the port structure 27. The mouth 52a, however, is constricted so that, as illustrated in FIG. 4a, it prevents the little finger of a typical adult user from being inserted into the cavity 52. The tip or end 44a of the needle is safely displaced inwardly from the open mouth 52a so that even if the user intentionally inserted his or her finger into the open mouth, the tip of the needle would not stick this finger. Typically, the open mouth 52a has a maximum width of no greater than about one centimeter, and the minimum distance between the mouth 52a and the tip 44a is about one centimeter.

The locking mechanism includes the threads 69a formed in the end 54 of the interior cavity wall 55 and the threads 69b in the exterior wall of the conduit 22. These threads 69a and 69b engage upon connection of the cap member 50 to the port structure 27 by screwing the cap member to the conduit 22. The top of the cap member 50 has a pair of outwardly extending wings 58 which facilitate screwing the cap member 50 to the conduit 22. As this is done, the interior wall 55, sliding over the exterior surface of the conduit 22, guides the needle 44 so that it penetrates the center of the seal 36. To further ensure that the needle 44 penetrates the center of the seal 36, the threads 69b could be lowered further beneath the seal so that the cap member would fit telescopically over the conduit 22 and then be screwed into position. Thus, the cap member 50, serving as the female component, and conduit 22, serving as the male component, mate in a male-female relationship, with the needle 44 always being housed safely within the center of the cavity in an unexposed condition and positioned to pierce the center of the seal 36.

A spindle 59 is provided to enable the cap member 50 to be screwed onto the port structure 27 without twisting the tube 48. This spindle 59 is received within an opening 61 within the cap member 50. The body of the spindle 59 has a cylindrical neck section with a groove 63 in an end which protrudes from the opening 61. The cylindrical body expands outwardly slightly to provide a shoulder 65 which engages a stop 66 when the spindle 59 is placed in the opening, and a TRU seal O-ring 67 is received in the groove 63 to hold the spindle in position but allowing the cap member to revolve about the spindle as it is screwed onto the port structure 27.

Along the longitudinal axis of the spindle 59 is a passageway 60. The tube 48 from the container 20 holding the medication is inserted into the one end 60a of the passageway 60 and is bonded to the internal surface of this passageway, for example, by means of an adhesive. The other end 60b of the passageway terminates in a threaded connector section 62 to which the needle 44 is secured. This needle has an adapter 64 which has an internal thread which engages the threads of the connector section 62. Thus, the needle 44 extends outwardly from this adapter 64. Thus, the needle 44 is held secure to the piggyback connector 16, penetrating the center of the seal 56 with its point 44a safely displaced away from the inside wall 55 of the conduit 22.

This connector 49 embodies many of the features of this invention. For example, the cap member 50 safely houses the needle 44, and the threads on the guiding walls provide means for detachably securing the cap member to the port structure without taping. But it has several components, and therefore is costly to manufacture, it is time consuming to screw the cap member 50 to the port structure, and it does not provide an audible signal when the cap member is safely secured to the port structure. This later feature is provided by the second and third embodiments of this invention.

Second Embodiment of the Invention

Figure 5:
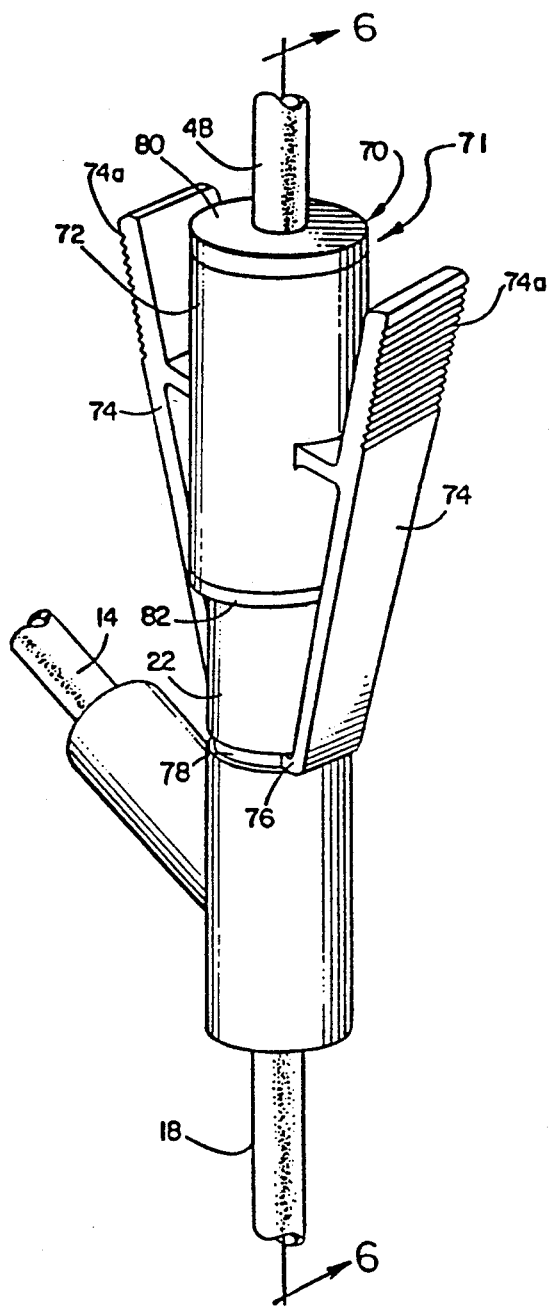
FIG. 5 is a perspective view of the second embodiment of the medical connector of the present invention which employs a snap-on type means for securing the cap member to the port structure.
Figure 6:
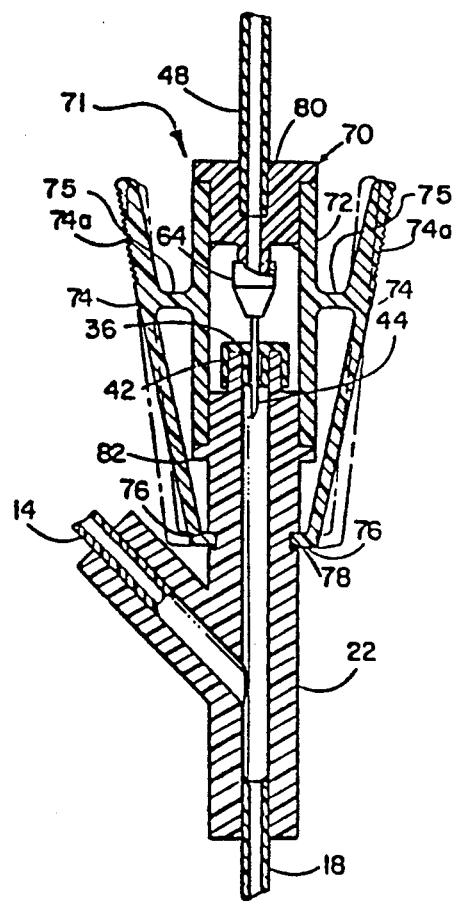
FIG. 6 is a cross-sectional view of the second embodiment of the medical connector of the present invention which employs a snap-on type means for securing the cap member to the port structure.

The second embodiment of the present invention, connector 71, is shown in FIGS. 5 and 6. In this embodiment a cap member 70, similar to cap member 50, is simply snapped onto the piggyback connector 16. The snap-on type locking mechanism of this connector 71 is easier to use and less costly to manufacture than the slip-on/twist type of the first embodiment.

In this embodiment, the cap member 70 includes a hollow cylindrical element 72 which carries on its exterior two clips 74 which have catch tips 76 that snap into a groove 78 in the external wall of the conduit 22. The clips 74 are mounted by hinges 75 to the element 72, and are integral with the element 72. A plug assembly 80 carries the tubing 48 and the needle 44, which is mounted on an adapter 64 such as shown in FIG. 4. This plug assembly 80 is glued or otherwise bonded to the open end of the cylindrical member 72. The cap member 70, including clips 74 and hinges 75, are molded from the same material, for example, nylon, which is a material having the desired resiliency.

To attach the cap member 70, one simply slips the member 70 over the conduit 22. The clips 74 bend outwardly slightly and, when the catch tips 76 of the clips are opposite the groove 78, the clips snap in place as shown in solid lines in FIG. 6. The centrally mounted needle 44 is guided into the center of the seal 36 by the cap member 70 which, like a telescope, slides over the tubular conduit 22. There is shoulder 82 which serves as a stop to limit the movement of the cap member 70. This shoulder 82 brings the catch tips 76 of the clips into registration with the groove 78. The hinges 75, being of the same material as the clips 74, provide an internal bias or spring action due to the resiliency of the material from which these clips and hinges are made. Consequently, the clips 74 snap into a locking position, locking the cap member to the conduit 22 when the catch tips 76 are in registration with the groove 78. To release the cap member from the piggyback connector 16, the clips 74 are simply depressed and the cap member 70 is removed.

One of the features of the slip-on type locking mechanism is that with one simple inwardly push, the needle 44 is inserted directly into the center of the seal 36 and the cap member is locked to the port structure. Another feature of this connector 71 is that when the tips 76 of the clips snap into the groove 78, a "click" sound is made by the tips striking the body of the cap member. With repeated use, however, the hinges 75, due to internal stress produced in the nylon material, lose some of their spring action. Consequently, the tips 76 are not held with sufficient force in the groove 78, nor do they strike the body of the cap member to produce the desired "click" sound. Moreover, the material will eventually crack along the flex line of the hinge and a break will occur. The reliability of this connector 71 is substantially improved by the third embodiment of this invention which employs a unique locking mechanism.

Third Embodiment of the Invention

Figure 7:
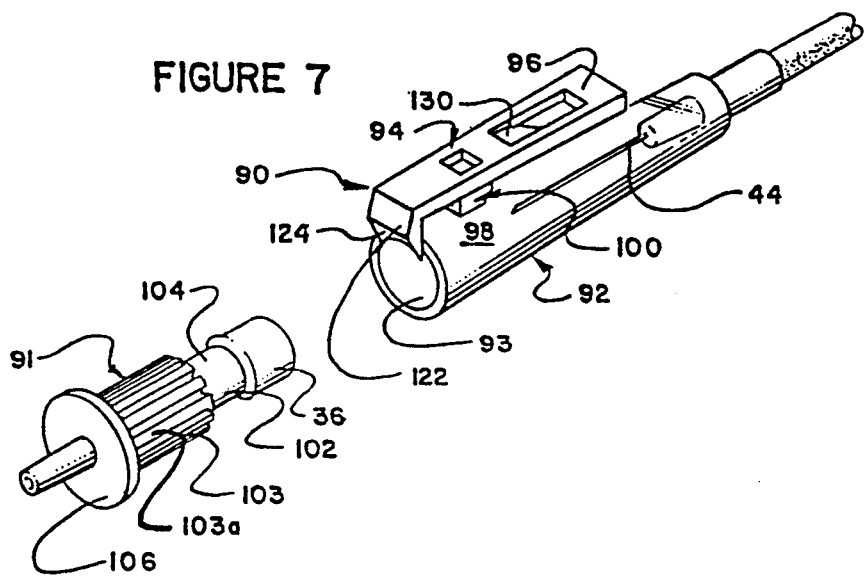
FIG. 7 is an exploded perspective view of the third embodiment of the medical connector of the present invention which employs a snap-on type means for securing the cap member to the port structure.

As shown in FIG. 7, the third embodiment of this invention, connector 90, includes a sealed port structure 91 and a cap member 92 having a locking mechanism 94 for detachably securing the cap member 92 to the port structure 91. The cap member 92 is similar to the cap members of the other embodiments and houses within its cavity 92a (FIG. 8) the needle 44. The cavity 92a has a tapered side wall 93 to better direct the needle 44 into the center of the seal 36.

The port structure 91 is a tubular conduit 102 having, at one end, a reduced diameter nipple 104 over which the seal 36 fits and, at the other end, a tapered barrel 103. The seal 36 is of the same type employed in conventional devices such as shown in FIG. 2. Material is removed from the barrel 103 to reduce cost. This results in the formation of flutes 103a in the barrel 103. At the base of the barrel 103, adjacent the end of the port structure 91, is an annular, disk-like piece which provides a lip 106. When the cap member 92 is placed over the port structure 91, a handle 96, which is a component of the locking mechanism 94, engages this lip 106. The handle 96 is hinged to the body 98 of the cap member by a two component hinge 100.

Figure 14:
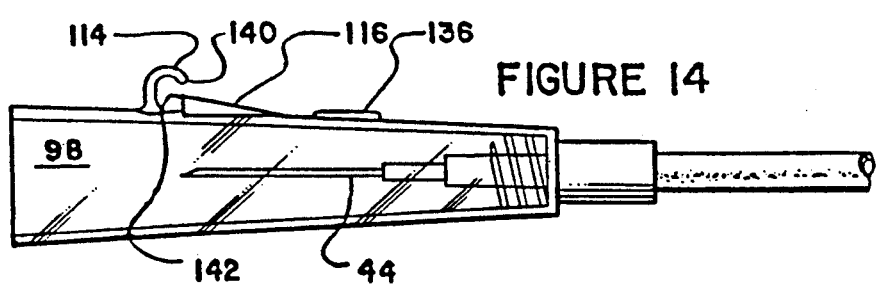
FIG. 14 is a side elevational view of the cap member with the handle of the locking mechanism removed.
Figure 15:
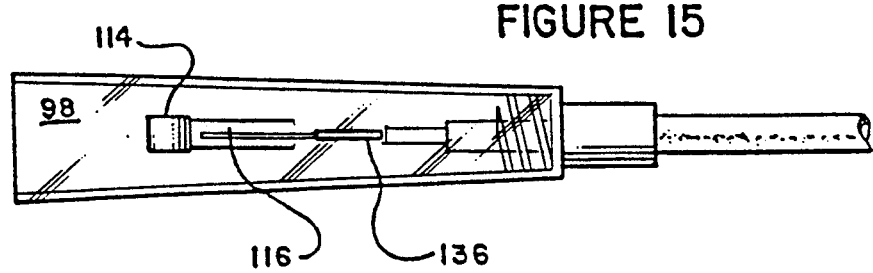
FIG. 15 is a top plan view of the cap member with the handle of the locking mechanism removed.

As best shown in FIGS. 14 and 15, a hook 114 is one component of the hinge 100 and the other component of the hinge is a crossrod 108 (FIG. 18) carried by the handle 96. The hook 114 projects outwardly from the body 98 of the cap member and has adjacent to it a ramp 116 which, as shown in FIG. 18, holds the crossrod 108 when the handle 96 is attached to the body of the cap member. A section of the crossrod 108 is cut away to provide a miter slot 118 which engages the ramp 116.

Figure 8:
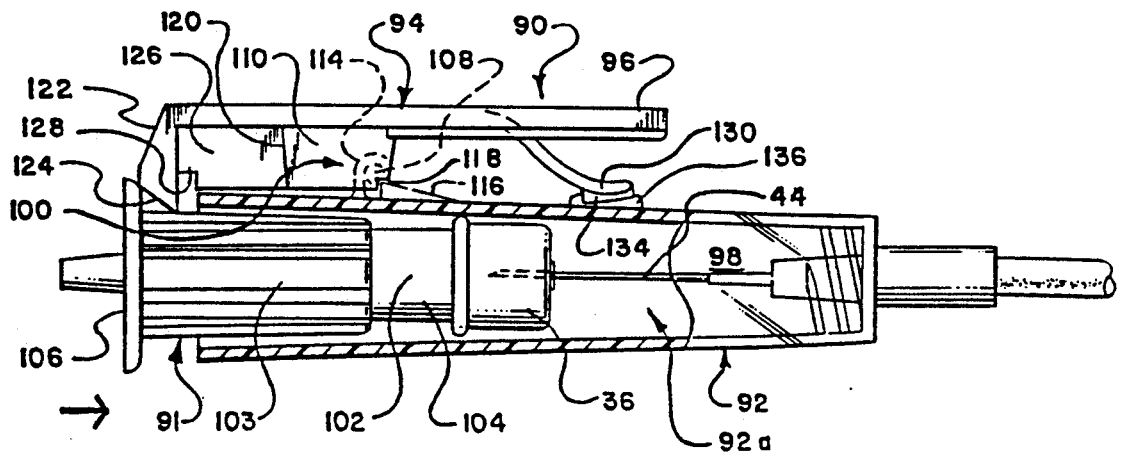
FIG. 8 is a side elevational view, with sections broken away, of the embodiment shown in FIG. 7. In this FIG. 8, the handle of the locking mechanism attached to the cap member just engages the lip of the port structure.
Figure 9:
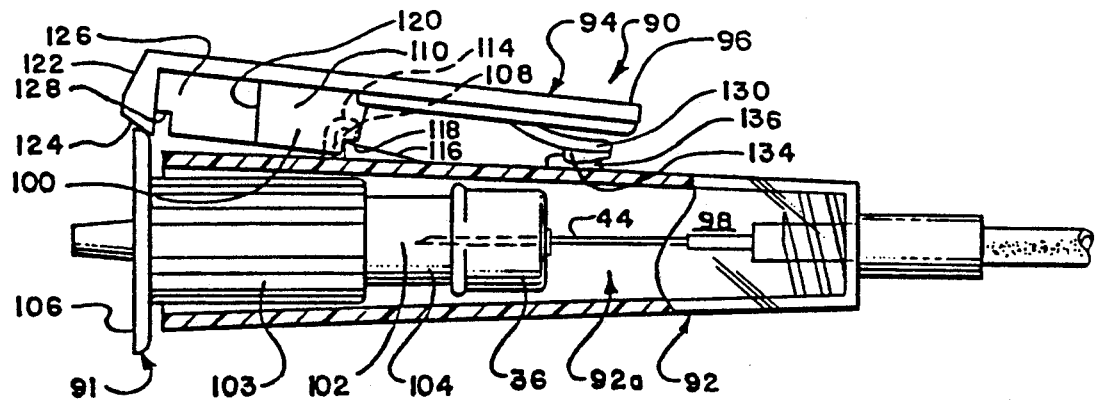
FIG. 9 is the same view as shown in FIG. 8, except the handle of the locking mechanism is flexed and just about to snap into locking engagement with the lip of the port structure.
Figure 10:
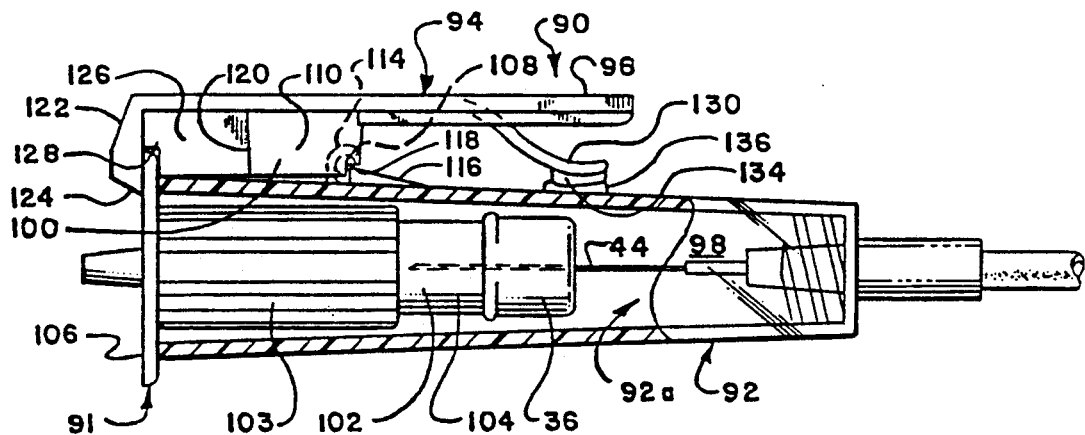
FIG. 10 is the same view as shown in FIGS. 8 and 9, except the handle of the locking mechanism is now engaging the lip of the port structure in the locking position.
Figure 10A:
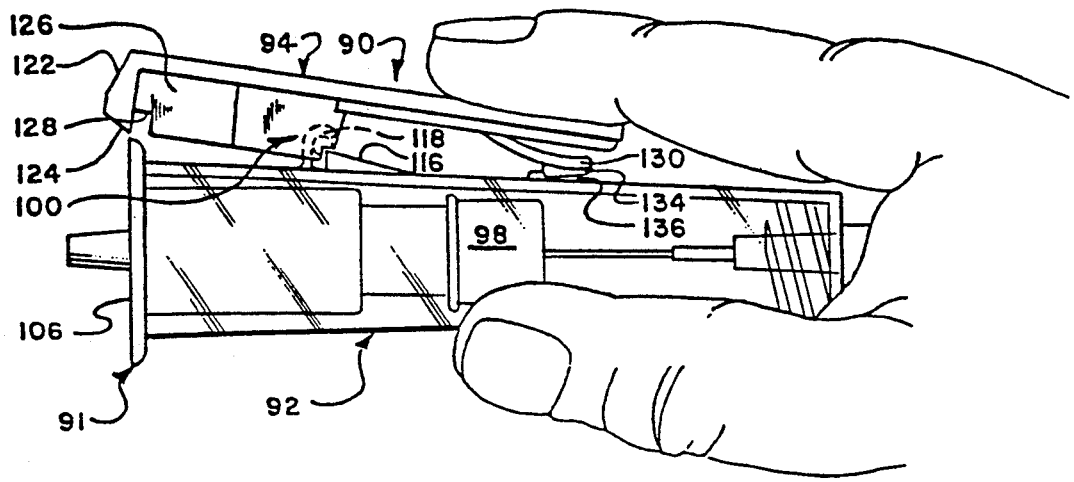
FIG. 10a is the same view as shown in FIGS. 8, 9 and 10, except the handle of the locking mechanism is flexed to permit removal of the cap member from the port structure.
Figure 11:
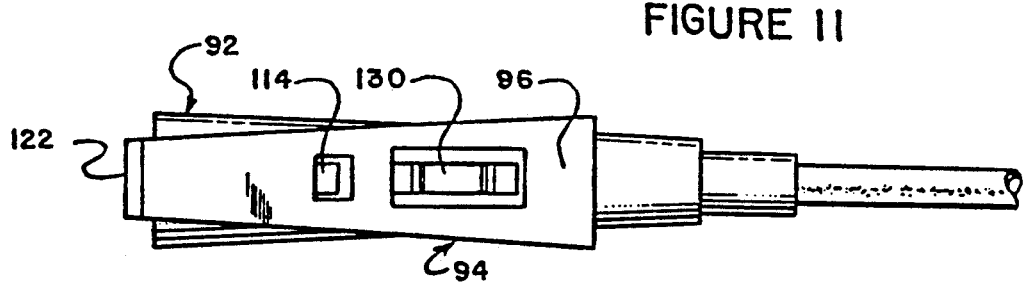
FIG. 11 is a top plan view of the cap member.
Figure 12:
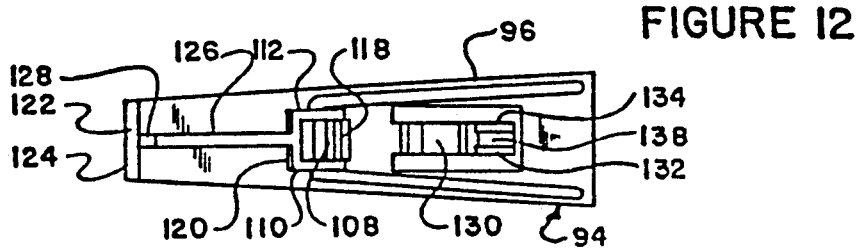
FIG. 12 is a bottom view of the handle of the locking mechanism shown in FIGS. 8 through 11.
Figure 13:
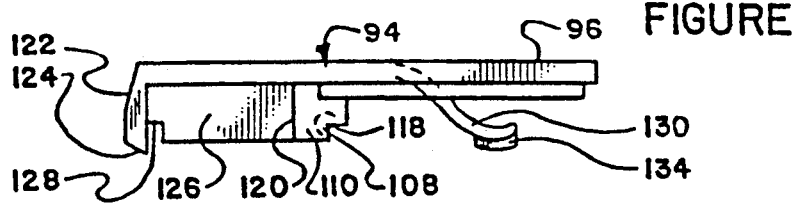
FIG. 13 is a side elevational view of the handle of the locking mechanism.

The handle 96 is best shown in FIGS. 12 and 13. It has a pair of spaced apart plates 110 and 112 extending downwardly from the underside of the handle and the crossrod 108 is disposed between these plates, with the opposed ends of the crossrod being integral with the plates. Opposite the crossrod 108 and parallel to it is a third plate 120, which is integral with the underside of the handle 96 and is at a right angle to and connects with the forward ends of the plates 110 and 112. Disposed on the underside of the handle 96 between the catch tip 122 and the plate 120 is a clapper bar 126. The clapper bar 126 produces the "click" sound when it strikes the body 98 of the cap member. This clapper bar 126 extends away from the plate 120 at a right angle and is integral, at one end of the handle, with the catch tip 122 and, at its opposite end, with the plate 120. The leading edge 124 of the catch tip 122 is beveled to facilitate the slippage of this tip up and over the lip 106, which is also beveled. At the point where the clapper bar 126 merges with the inside of the catch tip 122, there is a notch 128 which, as shown in FIG. 10, receives the lip 106 when the handle 96 is in the locking position. At the rear end of the handle 96 is a leaf spring 130 which has one end free and its opposed end integral with the handle 96. At the free end of the leaf spring 130 are two spaced apart tracks 132 and 134 (FIG. 12). When the handle 96 is attached to the body of the cap member as shown in FIGS. 8 through 10, a finger 136 on the body 98 of the cap member is received within the channel 138 between the tracks 132 and 134. On the underside of the handle 96 are two downwardly projecting reinforcing strips 140 and 142 (FIG. 12) which provide structural rigidity to the handle.

The way in which the handle 96 is pivotably connected to the cap member 92 by the two component hinge 100 is illustrated by FIGS. 16 through 19. To attach this handle 96 to the body 98 of the cap member, first one positions the handle over the body of the cap member opposite the hook 114 and then moves the handle into contact with the cap member so that the crossrod 108 touches the rear end of the ramp 116. The spring 130 is depressed at this time. Next, the handle 96 is moved towards the left, as shown in FIG. 17, with the crossrod 108 sliding up the ramp 116 until it engages the leading edge 140 of the hook 114. The dimension between the edge 142 of the ramp 116 and the edge 140 of the hook 114 is less than the diameter of the crossrod 108. Consequently, the hook 14 must flex slightly upwardly in a counterclockwise direction, as viewed in FIG. 17, until the crossrod 108 clears the edge 142 of the ramp and snaps into the position shown in FIG. 18. The hook 114 thus returns to the unflexed condition shown in FIG. 18, wrapping around the crossrod 108. The miter slot 118 then engages the edge 142 of the ramp, with this edge abutting the junction 118a of the slot 118 (FIG. 18). The ramp 116 thus holds the crossrod 108 in position, preventing the handle from becoming dislodged from the hook 114 and preventing the handle 96 from tilting to-and-fro about its longitudinal axis. When the handle 96 is so mounted to the body 98 of the cap member, the finger 136 slips into the channel 138 between the tracks 132 and 134 and holds the rear end of the handle so that it does not tend to move laterally. The handle 96 is, however, free to pivot about the hinge 100.

Unlike the hinges 75 of the second embodiment of this invention, the two component hinge 100 does not break due to fatigue. Thus, in accordance with one feature of connector 90, the handle 96 may be moved between a locked position (FIG. 10) and unlocked position (FIG. 8) as often as one wishes without breaking. At the same time, the handle 96, coating with the body 98 of the cap member 92, generates a "click" sound when the cap member is locked to the port structure 91. This "click" sound, as best illustrated in FIGS. 9 and 10, occurs when the handle 96 moves between the flexed position shown in FIG. 9 and the locked position shown in FIG. 10.

The connector 90 is highly reliable under actual hospital working conditions, and the way connector 90 is used is best shown in FIGS. 8 through 10a. First, the nurse inserts the end of the port structure carrying the seal 36 into the open mouth 93 of the cap member 92 to bring the lip 106 into engagement with the catch tip 122 of the handle 96 as shown in FIG. 8. As this is done, the tapered side wall 93 of the cap member and the tapered barrel 103 slide along each other to direct the needle 44 into the center of the seal 36. Simultaneously, the beveled edge 124 of the catch tip rides over the beveled lip 106 until the lip just engages the underside edge of this tip as shown in FIG. 9. This causes the handle 96 to rotate in a clockwise direction as viewed in FIG. 9, with the crossroad 108 turning while in the grasp of the hook 114. There is enough clearance between the miter slot 118 and the edge 142 of the ramp to allow the crossrod to turn sufficiently so the catch tip 122 clears the lip 106. Thus, the handle 96 pivots about the hinge 100, depressing the spring 130. With the handle 96 and lip 106 in this position, and the spring 130 depressed, as soon as the lip 106 clears the edged of the catch tip 122, the spring rotates the handle in a counterclockwise direction, moving it to the position shown in FIG. 10 with ample force so that the clapper bar 126 strikes the body 98 of the cap member to produce the "click" sound. This "click" sound is the audible signal which the nurse may rely upon to indicate that the cap member 96 is locked to the port structure 91. Under certain hospital conditions, particularly in the intensive care unit where there is not a great deal of light, this is an important feature because it provides additional assurance that the cap member 92 is locked to the port structure 91.

As shown in FIG. 10, with the handle 96 in this locked position, the needle 44 has penetrated the central portion of the seal 36, directed by the tapered sidewalls of the cavity 92a and the barrel 103. Medication now flows through the connector 90 into the patient. Note, the handle 96 is not depressed as the cap member 92 is slid over the port structure 91. To remove the cap member 92, the handle 96 is depressed, moving it to the position shown in FIG. 10a. With the handle 96 in this position, the cap member 92 is pulled off the port structure 91.

Except for the seal 36, the connector 90 is made entirely of a transparent plastic. The use of a transparent plastic is preferred because this allows the nurse to see that the needle 44 is correctly inserted into the seal 36, and thus provides additional safety. Also, the use of plastic makes the connector 90 a low cost, disposable item. The plastic most suitable is a polycarbonate made by Cyrolite Industries in Azusa, California sold under the trade name CYROLITE. This plastic, which is commonly employed to make medical devices, has been approved for such uses by the United States Federal Drug Administration.

The connector 90 is particularly adapted to be used in a variety of different applications. For example, as illustrated in FIG. 20, it may be connected directly in line with a container 144 of medication to be supplied intravenously to a patient. In this instance, the cap member 92 has a tube 146 extending from it which has at its one end a male component 148 of a conventional luer lock connector. This male component 148 engages and locks with a mating female luer component 150 attached to the end of a line 146 extending from the container 144. In a similar manner, the port structure 91 has extending from it a tube 154 which has at its end a female luer component 158 of a second luer lock connector. The male component 156 of this second luer lock connector is attached to the end of a tube 160 that is connected to a needle inserted into the vein of the patient. The luer lock connectors may be obtained from Burron Medical, Inc. in Bethlehem, Pennsylvania.

Figure 21:
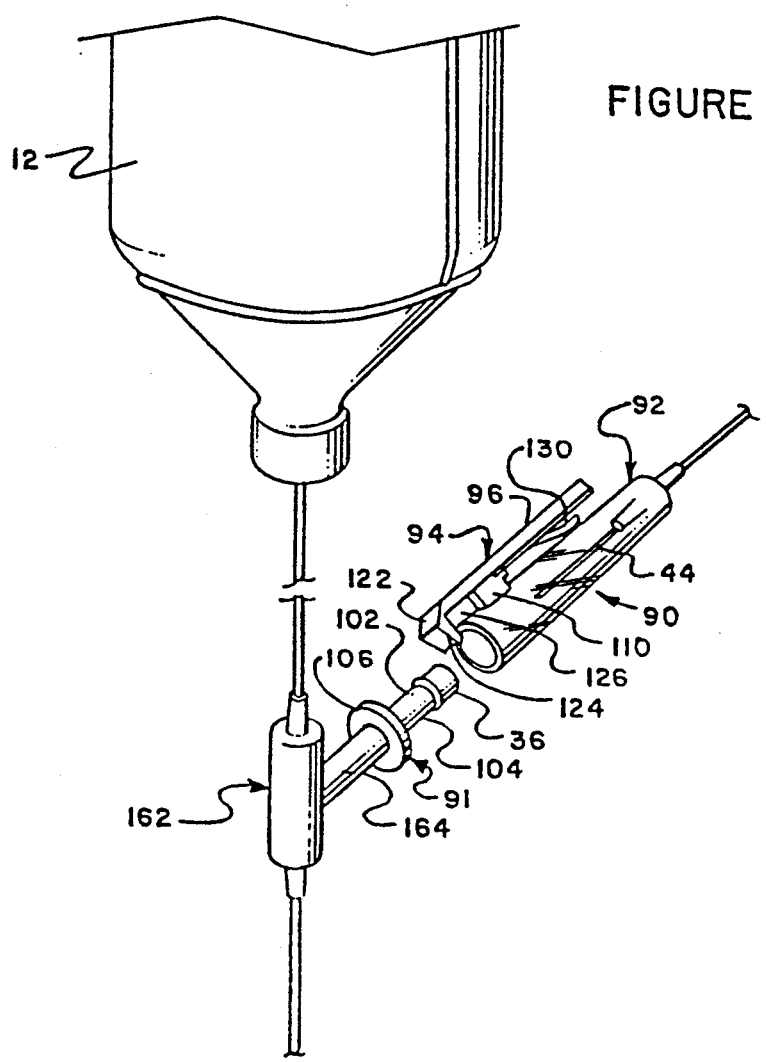
FIG. 21 is a perspective view of a medical connector like that shown in FIG. 7, except the port structure has the lip which engages the handle of the locking mechanism as an integral part of a conventional piggyback connector.

FIG. 21 illustrates the connector 90 integrated into a conventional piggyback connector 162. The branch line 164 from the piggyback connector 162 has attached to it and integral therewith the port structure 91 including the lip 106 that engages the catch tip 122 of the locking mechanism 94. Thus, a conventional feeding system 10 employing a piggyback connector may be modified by simply including a lip 106 adjacent the seal 36. This lip 106 will then serve as the site for detachably connecting the cap member 92 to the piggyback connector 162.

Figure 22:
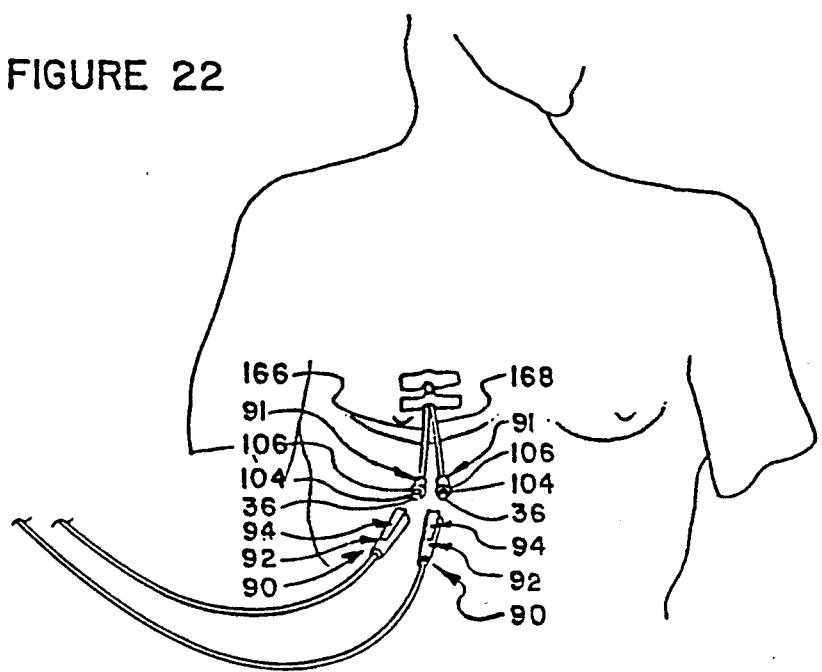
FIG. 22 is a schematic view showing a medical connector of the type shown in FIG. 7 designed to introduce medication into a patient's chest.

The connector 90, as shown in FIG. 22, also lends itself to be used with central venous catheters which are inserted into the chest of the patient. Frequently, patients under home care use such catheters, and consequently, even simpler and safer devices and techniques must be employed. However, a serious problem with such catheters is the way the ends of the lumens or tubes 166 and 168 extending from the patient are sealed. Presently, the ends of these tubes 166 and 168 are sealed using conventional luer locks. When it is time for the patient or the nurse to introduce medication into the catheter, an intermediate portion of the tubes 166 and 168 must be clamped while being connected to the source of medication so that air is not drawn into the blood stream of the patient. Any large intake of air into the patient's blood stream will seriously injure or even kill the patient. With children, even a small amount of air may be fatal. That is why clamps are used to close off the tubes 166 and 168 until the connection is made with the source of medication. This results in the tubes 166 and 168 wearing out, requiring that they be repaired. Not only is this a dangerous system, but it is extremely inconvenient for the patient or nurse to use.

As illustrated in FIG. 22, the connector system 90 overcomes these difficulties by simply having at each of the respective ends of the tubes 166 and 168 port structures 91. When the patient needs medication, he or she simply connects two of the cap members 92 to the respective port structures 91 and when finished, disconnects the cap members. The medication is fed by the needles 44 through the seals 36 and into the respective tubes 166 and 168. The cap members 92, when detached, withdraw the needles 44 from the seals 36, which are self-sealing. Thus I the nurse does not need to clamp off the tubes 166 and 168 nor is periodic repair of the tubes required. Since the seal 36 is self-sealing, upon removal of the cap member 92, there is no danger of air being drawn through the port structure 91 into the patient's blood stream. Consequently, connector 90 is both safer and more convenient to use than the conventional central venous catheters.

The connector 90 is also adapted to be used repeatedly without damaging the seal 36. Thus, it is even more suitable for applications as illustrated in FIG. 22 than conventional devices because of the accuracy with which the needle 44 may be repeatedly directed into the center of the seal 36. When the needle 44 is repeatedly stuck into and withdraw from the seal 36, the seal will have numerous holes in it and begin to develop a "swiss cheese"-like appearance. Eventually, a core is cut away from the seal by several of these holes interconnecting, rendering the seal useless because it is no longer self-sealing. Consequently, the seal would have a very short life. By carefully controlling the dimensions of the molds used to make connector 90, the cap member 92 and port structure 91 will be precision-made parts. Consequently, with repeated use, the needle 44 will essentially always penetrate the same hole in the seal 36, thus avoiding the "coring" problem.

Fourth Embodiment of the Invention

Figure 23:
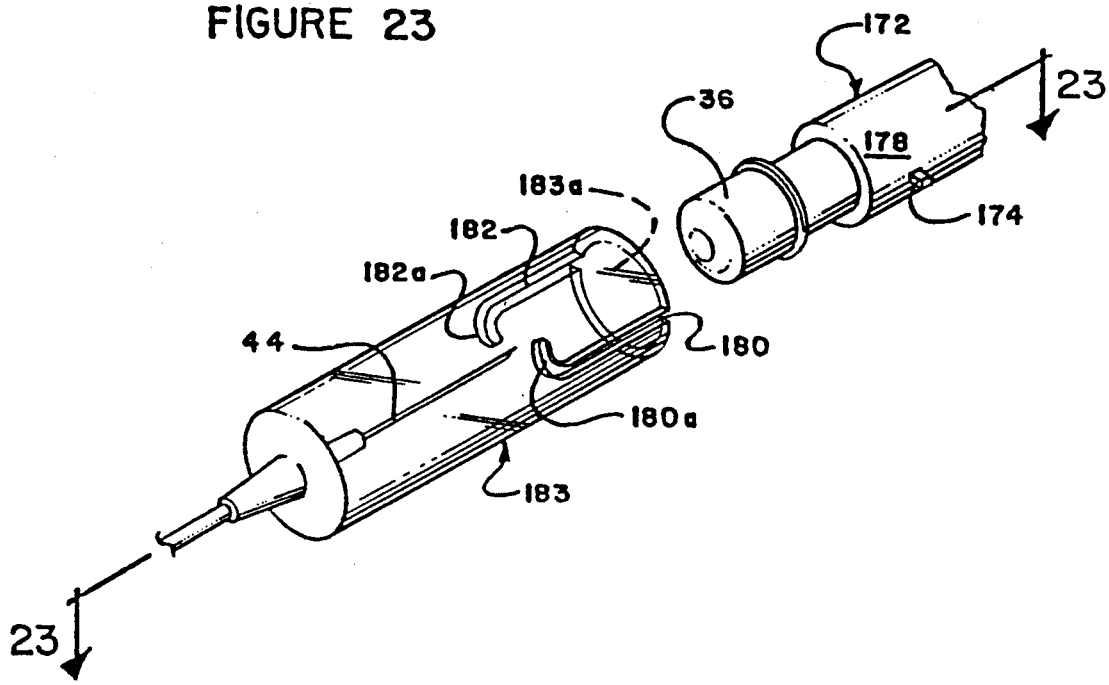
FIG. 23 is a perspective view of a fourth embodiment of the medical connector of this invention which employs a slip-on/twist lock type means for securing the cap member to the post structure.
Figure 24:
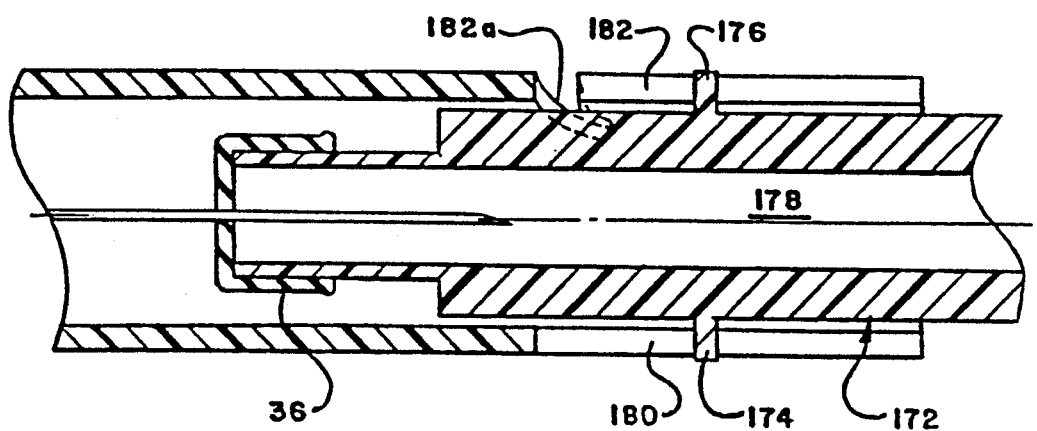
FIG. 24 is an enlarged cross-sectional view taken along line 24—24 of FIG. 23, showing the cap member being connected to the sealed entry port structure.

The fourth embodiment of this invention, the connector 170, is illustrated by FIGS. 23 and 24. In connector 170, the port structure 172 is similar to that shown in the other embodiments except it has a pair of pins on opposite sides of its body 178 which coact with J-type slits 180 and 182 in the sidewall of a cap member 183 housing the needle 44. These J-type slits 180 and 182 are opposed to each other and provide a guideway for the pins 174 and 176 which slide along these slits as the port structure 172 matingly engages the cap member 183.

To use this connector system 170, the nurse aligns the port structure 172 with the open mouth 183a of the cap member so that the pins 174 and 176 are in alignment with the entryway to the J-type slits 180 and 182. Then the nurse pushes the port structure 172 into the open mouth 183a, sliding the port structure into the cavity within the cap member 183. The pins 174 and 176 first engage the entryway of the J-type slits 180 and 182 and then slide along the slits until they reach the base of the slits. At this point, the nurse twists or rotates the cap member 183 and port structure 172 in counter-rotating directions so that the pins 174 and 176 will then slide respectively into the hooks 180a and 182a of the slits and be secured. This embodiment does not provide an audible signal upon locking the cap member 183 to the port structure 172, but is very economical to manufacture.

Function of the Cap Member and Port Structure

As will be appreciated from the above description, the cap member provides several functions in a single structure. (We will no longer refer by number to any one of the components of the invention since we are now discussing in general how the cap member and port structure function to provide the attributes of safety and convenience.) First, the cap member surrounds the needle and provides a housing in which the needle is lodged safely so that needle sticks are avoided. Second, because the needle is so lodged within the housing, if the nurse did, for example, lay the cap member on the patient's bed, the needle would not come into direct contact with the bedding which might be infested with harmful bacteria. Thus, this arrangement of the needle deep within the cavity in the cap member provides protection for the patient against bacterial contamination and protection for the nurse against accidental needle sticks.

The port structure also provides more than one function. First, it serves as the site to attach the cap member, and, by means of a simple locking element such as a lip, thread, groove, pin or the like, provides an economical way to modify the conventional piggyback connector so that it may be used with the cap member. Second, the combination of a self-sealing seal and adjacent element that locks the cap member provides a simple way to modify connectors so that they have enhanced safety and convenience.

The cap member and port structure function in combination to direct the needle into the center of the seal, lock these pieces together and enable quick connection. The nurse or patient simply aligns the sealed end of the port structure with the open mouth of the cap member and pushes the two pieces together. The internal wall of the cap member and the exterior wall of the port structure engage to align the two pieces so that their respective axes coincide, guiding the needle into the center of the seal as they are pushed together. Consequently, the needle does not scrape the inside wall of the port structure so that particles of plastic are not introduced into the patient's blood stream and the coring problem is virtually eliminated. The cap member and port structures each carry elements of a locking mechanism which engage and lock the pieces together when the needle has pierced the seal, preventing accidental disconnect. Although other geometric forms may be employed, quick connection is facilitated by the cylindrical configuration of the walls of the cap member and port structure and the circular open mouth of the cavity. In particular, the first through third embodiments of this invention are very quickly connected because no extra step is required to align the cap member and port structure. All that the nurse need do is insert the port structure into the open mouth without any special concern for their relative positions and, when using the second and third embodiments, simply push these two pieces together until the locking mechanism engages. When using the first or fourth embodiments, the extra step of rotating the two pieces relative to each other is required to engage the locking mechanism. When using the fourth embodiment, the pins must also first be aligned with the entryways to the J-slits prior to pushing the port structure into the cavity in the cap member.

Because of the features embodiment in the cap member and port structure, this invention may be used under normal hospital conditions without creating any additional work for the nurse, while substantially reducing the likelihood of harm to the patient due to carelessness and protecting the nurse against infection and making his or her job easier and faster.

Fifth Embodiment of the Invention

In a fifth embodiment of the invention it is further contemplated that the safety connector locking device contain a collar or ring-type rotating lock mechanism to secure the junction between the flexible intravenous drip tubing extending from the intravenous solution container and the "Y" or piggyback connector. The type of lock mechanism contemplated in this fifth embodiment of the invention is advantageously less expensive to manufacture and simpler to use than the previous embodiments. Like the previous embodiments, the device, of the fifth embodiment prevents needle sticks, protects the junction from contamination by adventitious agents and generates a "click" sound upon lock engagement.

Figure 25:
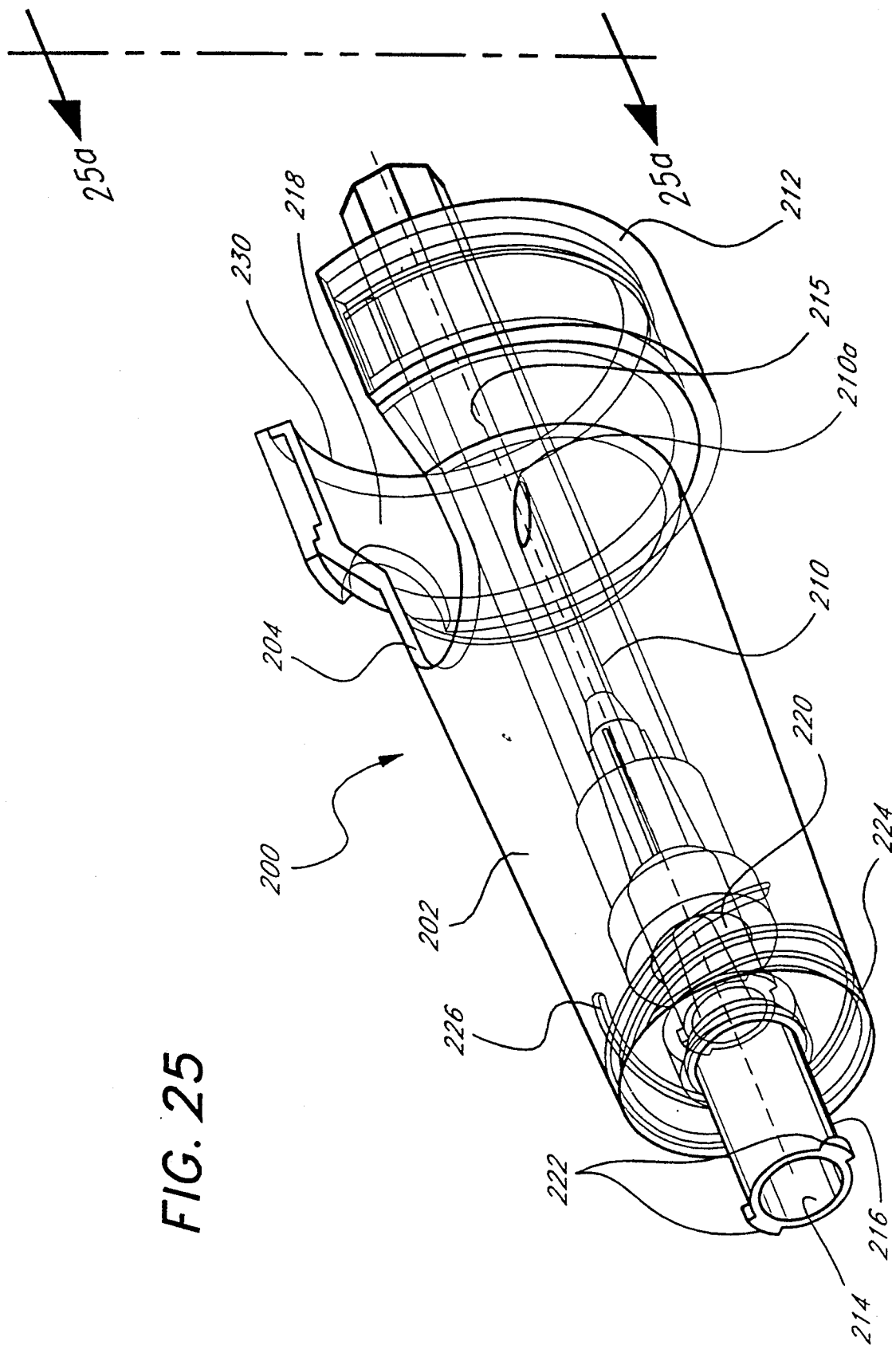
FIG. 25 is a perspective view of the fifth embodiment of the medical connector of the present invention which employs a twist lock means for securing the cap member to a port structure.

FIGS. 25-28 illustrate a preferred safety connector locking device. FIG. 25 illustrates perspective view in elevation of a preferred embodiment of the safety connector locking device 200. The locking device 200 is designed to fit over a "Y" or piggyback connector, such as the piggyback connector 16 diagrammed in association with FIG. 3. The safety locking device comprises a tubular body or cap member 202, an intravenous drip attachment tube 216 and a rotatable locking collar 212. The cap member 202 forms a hollow tubular chamber 218 that contains a needle 210 in open communication with a second chamber 214 to provide an open channel with the intravenous drip attachment tube 216. Fluid passes from the effluent intravenous drip tub 216 into chamber 214, through needle 210, and during engagement, into an influent port of the "Y" connector (not shown).

The cap member 202 is telescopically tapered with the widest portion at the locking collar 212 at the distal end of the device and narrowing toward the intravenous drip attachment tube 216 at the proximal end. The tapered cap member 202 serves to guide the piggyback connector conduit 22 (see FIG. 4) or branch port of the "Y" connector into the tubular chamber 218 so that the needle 210 pierces the septum or seal 36 on the conduit to actively engage the entry port of conduit 22, as depicted in FIG. 4, with the needle attachment region. Thus, the junction between the conduit and the safety connector device 200 is protected by the cap member 202 from exposure to adventitious agents.

The needle 210 is suspended from the needle attachment cap 220 such that the needle is centrally located with the tubular chamber. The overall length of the tubular chamber is such that the needle is recessed into the chamber. The widest portion of the cap member 202 is preferably narrow enough in cross sectional diameter and the needle 202 is recessed sufficiently such that the little finger of a typical adult user cannot enter the tubular chamber and contact the suspended needle. Preferably the widest portion at the opening, of the tubular chamber 218 is no greater than about one centimeter and the minimum distance between the opening and the needle tip 210a is at least about one centimeter. However, varying conduit or branch port diameters of the "Y" connector with which the apparatus is used may necessitate slight changes in the diameter of the apparatus 200.

Beginning at the tubular intravenous drip IV attachment tube 216, there are two attachment barbs 222 that extend outwardly from the drip attachment tube. These barbs 222 provide attachment holds for the flexible intravenous drip tubing that extends from the medication container and ends at the safety connector locking device (see FIG. 1). Preferably the barbs 222 form a male luer connector for attachment onto intravenous tubing, however other attachment means are contemplated. These would be well known to those individuals with skill in the art, thus no additional discussion is required. It is further contemplated that an adhesive could be used to strengthen the attachment between the flexible intravenous drip tubing and attachment tube 216. The second open chamber 214 permits the continuous flow of liquid from the medication chamber through the safety connector and into the Y connector. Dashed line 215 indicates the continuous opening provided from tubular chamber 214 through the distal region of the cap member 202.

The terms "lower" and "distal" are used in association with the fifth embodiment to describe that portion of a given element of the invention that is in spatial proximity to the "Y" connector during use. The terms "upper" and "proximal" are spatially defined as that portion of a given element of the invention that is more proximate to the medication container during use. Thus intravenous IV drip attachment tube 216 is connected to the upper rim 224 of cap member 202 and is situated at the proximal end of the apparatus. In this embodiment piggyback connector locking device 212 is associated with the lower rim 230 or distal portion of cap member 202.

Intravenous drip attachment tube 216 enters through the upper rim of the cap member into tubular chamber 218. The attachment tube 216 telescopically narrows within the tubular chamber toward needle 210 to form a needle attachment site. Needle attachment cap 220 is connected to needle 210 at its proximal end. The needle attachment site is an extension of the intravenous drip attachment tube that extends into tubular chamber 218. Needle attachment cap 220 preferably connects to attachment tube 216 by a luer-lock fitting. Threads 226 within the tubular chamber facilitate the fitting between the cap member 202 and needle 210. It is additionally contemplated that an adhesive could be used to strengthen the fitting between the needle attachment cap and the distal portion of the attachment tube. Other attachment mechanisms are contemplated and the preferred examples described herein are in no way intended to limit the scope of this embodiment. Along the length of the cap member and extending toward the distal rim 230 is cap member archway 204. The archway comprises a cut out section along the lower wall of the cap member casing to provide a channel or slot for one arm of the "Y" connector. Piggyback connectors often are formed in the shape of a "Y". These connectors have a straight tubular portion and a lateral arm extending outward. The "Y" has two arms or branches joining at a crook to form a "V". Each branch forms an influent fluid conduit that is sealed by a pierceable septum. A stalk extending from the crook joins both conduits into a single influent fluid line. During use, one arm of the "Y" is inserted into the cap member of the disclosed invention. Archway 204 forms a channel or slot for the adjacent arm. The archway fits into the crook to create a snug fit such that the proximal portion of the archway sits within the crook formed by the two branches of the Y. This permits the distal end of the safety connector to extend around the adjacent arm and extend down the stalk of the connector.

With the archway facing the crook of the "Y" connector, it is possible to lock the safety connector 200 in place following needle engagement. Included in the fifth embodiment of the disclosed invention is a rotatable locking collar 212 that forms a twistable annular collar that glides about the lower rim of the cap member.

FIG. 26 is an exploded elevational view of FIG. 25. Cap member 202 is separated from the rotatable locking collar 212. In a preferred embodiment, the cap member 202 has a shoulder extension 232 that further broadens the telescopic expansion of the cap member. The width of the lower edge 234 of the shoulder 232 defines the final external width of the safety connector device. Preferably, the distance along the cap member between the lower edge of the shoulder and the distal rim of the cap member 230 defines the height of the rotatable locking collar 212.

With the exception of two cut out regions, the collar locking device comprises an essentially circular ring that is preferably manufactured from the same material as the cap member. The first cut out region of the locking collar, defined as the area between edges 236 and 240, is preferably equal in width to the cap member archway 204 such that in the open or first position (see FIG. 27), the collar and archway are superimposed. The rotatable locking collar is sized just larger than the distal portion of the cap member to permit rotation about a common axis. The collar locking device has a second cut out notch 242 that will be discussed in further detail below.

The distal rim 230 of the cap member has an annular shoulder or slight lip extension 244 that serves as a distal rotation guide for the collar locking device. In addition a second rotational guide 246 is preferably formed as a groove immediately below the lower edge 234 of the cap member shoulder 232. A locking bar 248 is provided along one edge of the archway opening on the cap member and a complementary locking bar 250 is additionally positioned along edge 236 of the collar locking device 212.

Figure 25B:
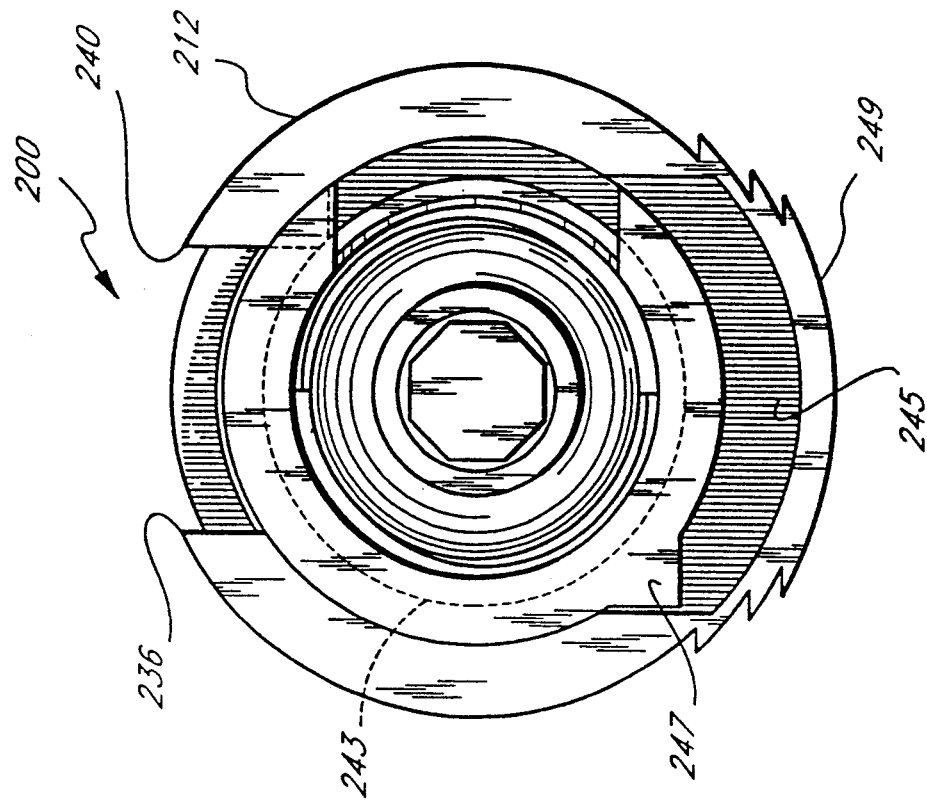
FIG. 25b is a planar view of the distal end of the embodiment shown in FIG. 25 with the locking collar in the closed, locked position.
Figure 25A:
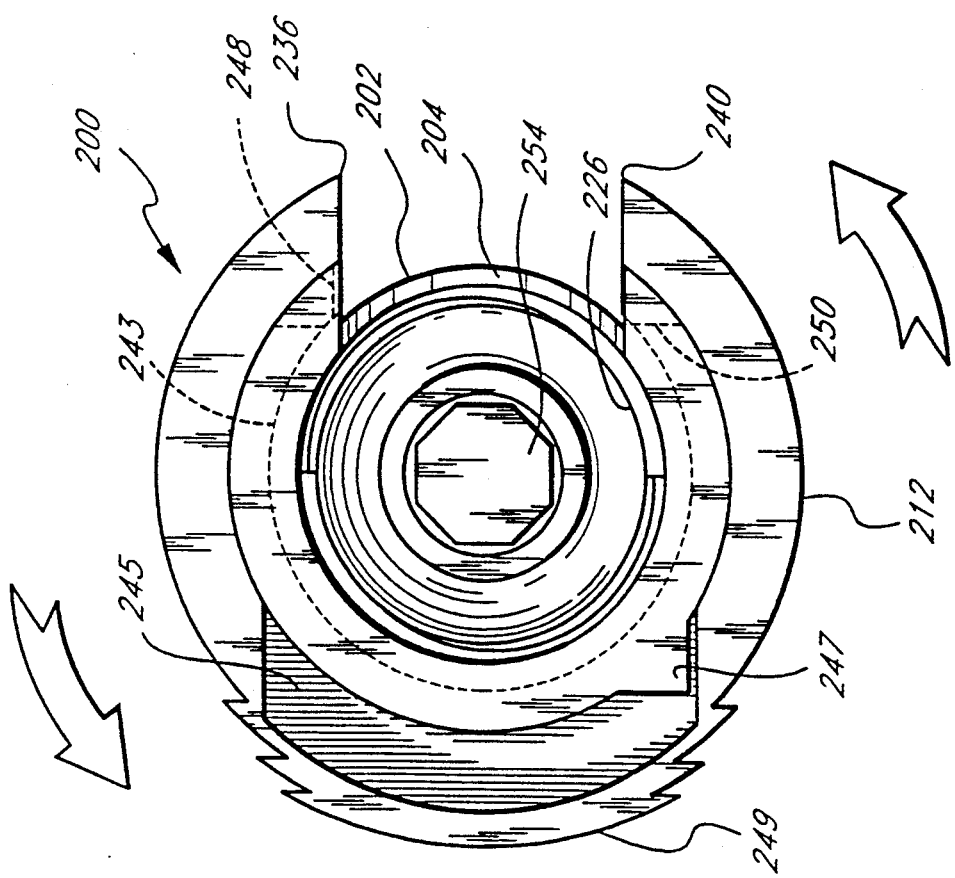
FIG. 25a is a planar view of the distal end of the embodiment shown in FIG. 25 with the locking collar in the open position.
Figure 27:
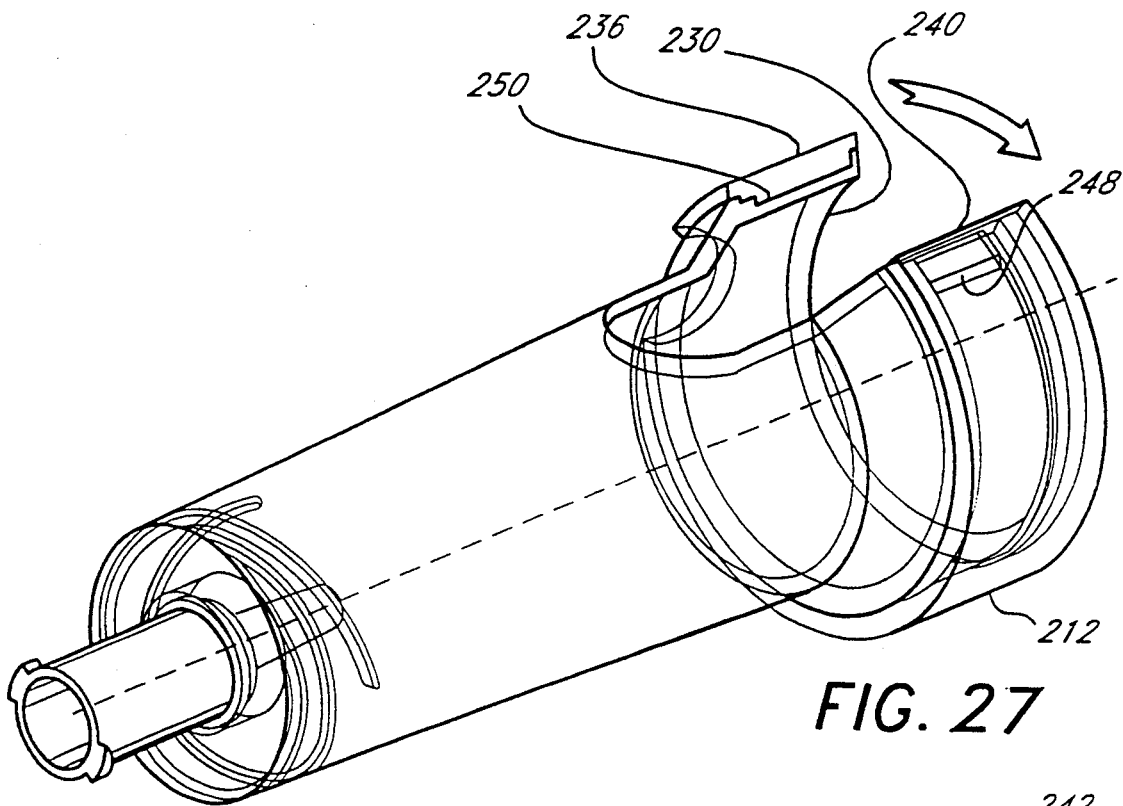
FIG. 27 is a perspective view of the cap member of the embodiment shown in FIG. 25, with the locking collar in the open position.

Thus, the collar locking device is designed to fit beneath cap member shoulder edge 234 along the rotational guides such that it can rotate around the distal region of the cap member. Annular flange 243 extends radially inward from the collar locking device and follows the cap member lip extension guide 244. As best seen in FIGS. 25a and 25b, and also in FIGS. 27 and 28, rotation from a first position (see FIGS. 25a and 27) is unidirectional toward edge 240 and is restricted by a radially outward extending stop 247 located circumferentially on the outer surface of rim 230. The collar is permitted to rotate within a recessed region 245 of annular flange 243. In the open position, as shown in FIGS. 25a and 27, locking bar 248 on the cap member is opposite complementary locking bar 250 and outward extending stop 247 is positioned along the recessed region 245 proximal to stop bar 250.

Figure 28:
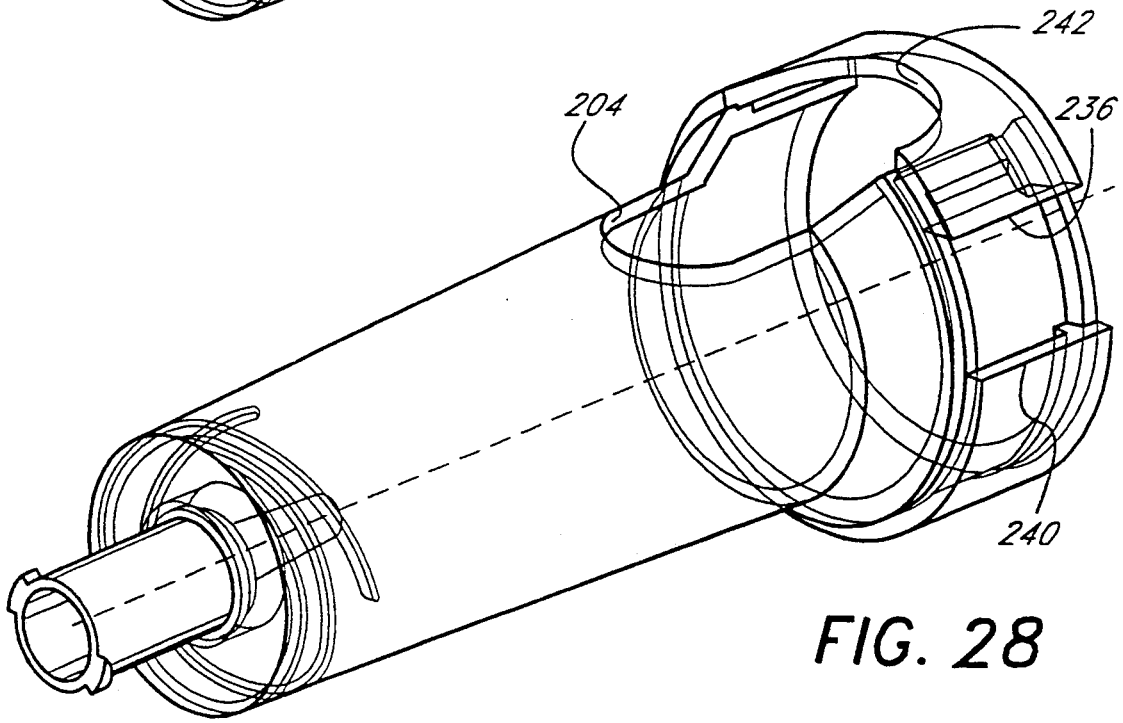
FIG. 28 is a perspective view of the cap member of the embodiment shown in FIG. 25, with the locking collar in closed, locked position.

To close, the collar locking device is rotated toward locking bar 248 (see FIGS. 25b and 28). Additional rotational pressure is required to pass complementary locking bar 250 past locking bar 248 to produce an audible "click". This noise tells the operator that the device is positioned correctly on the "Y" connector. A recess 248 adjacent to locking bar 250 receives the bar 250 and the outward extending stop 247 moves to a position along recessed region 245 proximal to collar edge 240. In the locked position, diagramed in FIGS. 25b and 28, the cut out notch 242 moves beneath archway 204 to provide a locked oval channel or slot to accommodate the arm of the Y connector not actively engaged by the disclosed invention.

As seen in FIGS. 25a and 25b, and also in FIG. 26, the rotatable collar 212 is provided with a handle 249 which allows the user of the device to easily grasp the collar 212 for rotation in accordance with the foregoing description. In the embodiment shown, the handle 249 comprises a raised ridge on the collar 212. However, other handles, such as a tab extending from the collar 212, are contemplated within the context of the present invention.

As best seen in FIG. 26, the needle attachment cap 220 is preferably supplied with two or more barbs 252. These engage needle attachment threads 226 in a luer-lock type locking mechanism. The apparatus additionally comprises a needle sheath 254. Thus the safety connector locking device 200 is provided for use as a sterile product that could additionally be provided with or without sterile intravenous drip tubing.

During use, the device 200 is removed from its sterile packaging. Tubing is connected via barbs 222 onto the intravenous drip attachment tube. Needle 210 is secured to the casing chamber portion of the attachment tube 216 by turning the protective sheath 254 to the right. The needle sheath 254 is removed by pulling outward. The pierceable septum over the "Y" connector conduit is swabbed with alcohol to decontaminate the puncture site. The cap member is slid over the branch of the Y connector that has been swabbed. Archway 204 is aligned with the crook of the "Y" connector and the cap member is pushed onto the arm of the Y connector as far as it will go or until the collar locking device can be rotated to form an enclosure around the stalk of the "Y" connector. Needle 210 should pierce the septum during the connection procedure. The collar 212 is rotated until it locks. In the preferred embodiment, a "click" sound will be heard upon locking due to the locking bar 250 going into the recess 248. Preferably, the drip medication is allowed to flush through the apparatus prior to connecting the intravenous drip to the patient's arm. However this is not always possible, particularly when the intravenous connection is already in place. Thus, the prior flushing step can be omitted.

The addition of the safety connector to the "Y" connector can be accomplished quickly and precisely without risk of needle puncture or improper insertion in to the arm conduit since the telescopic design guides the cap member to the proper location and the cap member covers the needle tip.

The device has minimum removable pieces and is therefore more cost effective to manufacture. It is easy to use and has a low risk for contamination and needle sticks. An audible signal insures that the lock mechanism is in place.

RECAPITULATION OF THE INVENTION

In recapitulation: our connector is safe because (a) the needle is recessed deeply within the cap member and, therefore, is not likely to be contaminated by bacteria; (b) the cap member and port structure upon engagement guide the needle into the center of the seal, avoiding scraping particles from the inside wall of the port structure; (c) the cap member, housing the needle safely within it, protects the nurse against needle sticks; (d) the locking of the cap member and port structure together prevents accidental disconnects; and (e) the "click" signals the nurse when the connector system is locked securely in position. Our connector is convenient to use because (a) the walls of the cap member and port structure, interacting with each other, provide a guideway for quick connection; (b) the locking mechanism eliminates the burdensome and time consuming task of taping; and (c) the connector is very simple to use so that it is ideal for home care of patients.

SCOPE OF THE INVENTION

The above description presents the best mode contemplated of carrying out the present invention as depicted by the five embodiments disclosed. The combination of features illustrated by these embodiments provide the safety and convenience of this invention. This invention is, however, susceptible to modifications and alternate constructions from the embodiments shown in the drawing and described above. Consequently, it is not the intention to limit it to the particular embodiments disclosed. On the contrary, the intention is to cover all modifications and alternate constructions falling within the scope of the invention as generally expressed by the following claims:

We claim:

1. A safety connector for placing an influent fluid line in fluid communication with an effluent fluid line, said effluent line having a pierceable septum thereon and a projection extending radially therefrom proximate the pierceable septum, said connector comprising:

an elongate tubular body having proximal and distal ends and an interior and exterior surface, said proximal end comprising a first male luer connector on the exterior of said body at said proximal end and a second luer connector located in the interior of said tubular body at said proximal end;

a needle removably disposed in the tubular body, said needle having a proximal attachment end and a sharpened distal end, the proximal end of said needle formed into a hub for connection to said second luer connector located on the interior of said tubular body at the proximal end of said tubular body, and said needle extending in the distal direction within said tubular body wherein said distal end of said needle is disposed a sufficient distance from the distal end of said tubular body such as to substantially prevent contact between the distal end of said needle and the fingers of an operator handling said safety connector;

a slot in the wall of said tubular body extending axially from said distal end in the direction of said proximal end, said slot adapted to receive the projection on said fluid line;

a rotatable collar having inward and outward facing surfaces, said collar disposed on the distal end of said tubular body and adapted to rotate between first and second positions, said first position being such that a discontinuity on the rotatable collar aligns with said slot in the wall of said tubular body thus providing an axially extending slot for receiving said projection in an axial direction, said second position being where said discontinuity is rotated out of alignment with the slot in the wall of said tubular body, thereby preventing axial withdrawal of said effluent fluid line, and thus preventing removal of said needle from engagement with said pierceable septum, and said rotatable collar positioned on said tubular body such that when said projection is accepted and said collar is rotated into said second position, said rotatable collar contacts said projection at a distance from the point where said projection and effluent line join, said collar also having a radially extending, inwardly facing axially oriented ridge, a radially inwardly extending annular flange, and a circumferential channel on the radially inwardly facing surface of said collar;

a recess on said tubular body for receiving said radially extending, axially oriented ridge on said collar when said collar is in said second position, said ridge producing an audible click when said collar is rotated into the second position;

a substantially cylindrical surface on the exterior distal end of said tubular body for slidably receiving said rotatable collar;

an annular shoulder on said cylindrical surface for receiving said radially inwardly extending annular flange on said rotatable collar to rotatably secure said collar to said surface; and a radially outwardly extending stop located on the substantially cylindrical surface on the exterior distal end of said tubular body, said stop designed to be recieved in said circumferential channel on said inwardly facing surface of said rotatable collar, the stop and channel cooperating so that the range of rotation of said rotatable collar with respect to said tubular body is limited.

2. The connector of claim 1, additionally comprising outwardly axially extending ridges positioned in one area on the outside of said rotatable collar, whereby fingers of a user can readily engage said collar for rotation.

* * * * *